US010777321B2

(12) United States Patent
Shetty et al.

(10) Patent No.: US 10,777,321 B2
(45) Date of Patent: *Sep. 15, 2020

(54) SYSTEM AND METHOD FOR FACILITATING DELIVERY OF PATIENT-CARE

(71) Applicant: CURA TECHNOLOGIES INC., Saratoga, CA (US)

(72) Inventors: Devi Prasad Shetty, Bangalore (IN); Samir Mitra, Saratoga, CA (US)

(73) Assignee: CURA TECHNOLOGIES INC., Saratoga, CA (US)

( * ) Notice: Subject to any disclaimer, the term of this patent is extended or adjusted under 35 U.S.C. 154(b) by 17 days.

This patent is subject to a terminal disclaimer.

(21) Appl. No.: 16/167,015

(22) Filed: Oct. 22, 2018

(65) Prior Publication Data

US 2019/0057776 A1 Feb. 21, 2019

Related U.S. Application Data

(63) Continuation of application No. 14/335,815, filed on Jul. 18, 2014, now Pat. No. 10,109,377.

(30) Foreign Application Priority Data

Dec. 3, 2013 (IN) .......................... 5563/CHE/2013
Dec. 3, 2013 (IN) .......................... 5564/CHE/2013

(51) Int. Cl.
*G16H 50/20* (2018.01)
*G16Z 99/00* (2019.01)
(Continued)

(52) U.S. Cl.
CPC ............. *G16H 50/20* (2018.01); *G06F 19/00* (2013.01); *G16Z 99/00* (2019.02); *G06F 19/328* (2013.01);
(Continued)

(58) Field of Classification Search
CPC ........ G16H 50/20; G16H 20/10; G16H 40/20; G16H 20/40; G16H 20/17; G16Z 99/00;
(Continued)

(56) References Cited

U.S. PATENT DOCUMENTS 7,287,031 B1 10/2007 Karpf et al.
2002/0120471 A1 8/2002 Drazen
(Continued)

FOREIGN PATENT DOCUMENTS

JP 11242702 A 9/1999
JP 2001-005585 A 1/2001
(Continued)

OTHER PUBLICATIONS

How are you?, Cambridge Healthcare [online] [retrieved Jul. 22, 2014] URL: https://en-gb.howareyou.com/.
(Continued)

*Primary Examiner* — Jonathan Durant
*Assistant Examiner* — Chad A Newton
(74) *Attorney, Agent, or Firm* — Procopio, Cory, Hargreaves & Savitch LLP

(57) ABSTRACT

A computer-implemented method for facilitating delivery of patient-care in adherence with a standard of care clinical protocol is described. The method includes monitoring, by a computing device, patient information indicative of a clinical condition, based on a clinical protocol that comprises patient-care instructions that must be completed within a time period. The method further includes providing, by the computing device, the patient-care instructions to a user based on a result of the monitoring. The method also includes determining, by the computing device, adherence to the clinical protocol based on a result of at least one of the providing patient care instructions and the patient information; and for a determination that the clinical protocol has
(Continued)

not been adhered to, providing a recommended action request that calibrates the patient care instructions in compliance with the clinical protocol.

20 Claims, 14 Drawing Sheets

(51) Int. Cl.

| | |
|---|---|
| ***G06F 19/00*** | (2018.01) |
| *G16H 20/17* | (2018.01) |
| *G16H 20/40* | (2018.01) |
| *G16H 40/20* | (2018.01) |
| *G16H 20/10* | (2018.01) |

(52) U.S. Cl.
CPC ...... *G06F 19/3456* (2013.01); *G06F 19/3481* (2013.01); *G16H 20/10* (2018.01); *G16H 20/17* (2018.01); *G16H 20/40* (2018.01); *G16H 40/20* (2018.01)

(58) Field of Classification Search
CPC .... G06F 19/00; G06F 19/328; G06F 19/3481; G06F 19/3456
See application file for complete search history.

(56) References Cited

U.S. PATENT DOCUMENTS

| | | | |
|---|---|---|---|
| 2004/0064342 | A1 | 4/2004 | Browne et al. |
| 2007/0150024 | A1 | 6/2007 | Leyde et al. |
| 2008/0243549 | A1* | 10/2008 | Woronka ............... G06Q 50/24 705/3 |
| 2009/0132586 | A1 | 5/2009 | Napora et al. |
| 2009/0299766 | A1 | 12/2009 | Friedlander et al. |
| 2010/0121170 | A1 | 5/2010 | Rule |
| 2011/0040247 | A1 | 2/2011 | Mandro et al. |
| 2011/0112442 | A1 | 5/2011 | Meger et al. |
| 2011/0264696 | A1 | 10/2011 | Selaniko |
| 2012/0035959 | A1 | 2/2012 | Berdia |
| 2012/0078062 | A1 | 3/2012 | Bagchi et al. |
| 2012/0129139 | A1 | 5/2012 | Partovi |
| 2012/0154582 | A1 | 6/2012 | Johnson et al. |
| 2012/0172674 | A1 | 7/2012 | Welz et al. |
| 2012/0265547 | A1 | 10/2012 | Hwang et al. |
| 2012/0316897 | A1 | 12/2012 | Hanina et al. |
| 2013/0268282 | A1 | 10/2013 | Hugo et al. |
| 2013/0268891 | A1 | 10/2013 | Finley et al. |
| 2013/0282405 | A1 | 10/2013 | Van Zon et al. |
| 2013/0304493 | A1 | 11/2013 | Partovi |
| 2014/0088192 | A1 | 3/2014 | Heller et al. |
| 2014/0114673 | A1 | 4/2014 | Hu et al. |

FOREIGN PATENT DOCUMENTS

| | | | |
|---|---|---|---|
| JP | 2007-531079 | A | 11/2007 |
| JP | 2009514061 | A | 4/2009 |
| JP | 2012-123552 | A | 6/2012 |
| KR | 1020080013129 | A | 2/2008 |
| WO | 2005114524 | A2 | 12/2005 |

OTHER PUBLICATIONS

Healthcare IT News, An App Store for Healthcare Pros, Jan. 10, 2012, 3 pgs., [online] [retrieved Jul. 22, 2014] URL: https://www.healthcareitnews.news/app-store-healthcare-pros.

NHS Choices Health Apps Library, 1 pgs. [online] [retrieved Jul. 22, 2014] URL: https://apps.nhs.uk/.

Yuan, M.J., Evaluation of User Interface and Workflow Design of a Bedside Nursing Clinical Decision Support System, Interactive Journal of Medical Research, 2013, 2(1), 15 pgs.

International Search Reporting and Written Opinion for PCT/US2014/067968, dated Mar. 24, 2015, 11 pgs.

Extended European Search Report for related EP App No. 14868138.0 dated Mar. 29, 2017, 11 pgs.

Office Action for related TW App No. 103140957 dated May 22, 2018, 15 pgs.

Notice of Rejection for related JP App. No. 2016-536179, dated Jun. 11, 2019, 6 pages.

Notice of Rejections for related JP App No. 2016-536179 dated Oct. 16, 2018, 9 pgs.

* cited by examiner

| | Chest Drainage Indicating Reoperation | | | | |
|---|---|---|---|---|---|
| | Hourly Amount (mL/Hr) | | | Total Amount (mL) | |
| | No. of Successive Hours | | | Hour No. | |
| Preoperative Weight (kg) | 1 | 2 | 3 | 4 | 5 |
| 5 | 70 | 60 | 50 | 120 | 130 |
| 6 | 70 | 60 | 50 | 130 | 155 |
| 7 | 70 | 60 | 50 | 150 | 180 |
| 8 | 90 | 70 | 50 | 175 | 200 |
| 9 | 90 | 80 | 60 | 195 | 230 |
| 10 | 100 | 90 | 65 | 220 | 260 |

FIG. 4

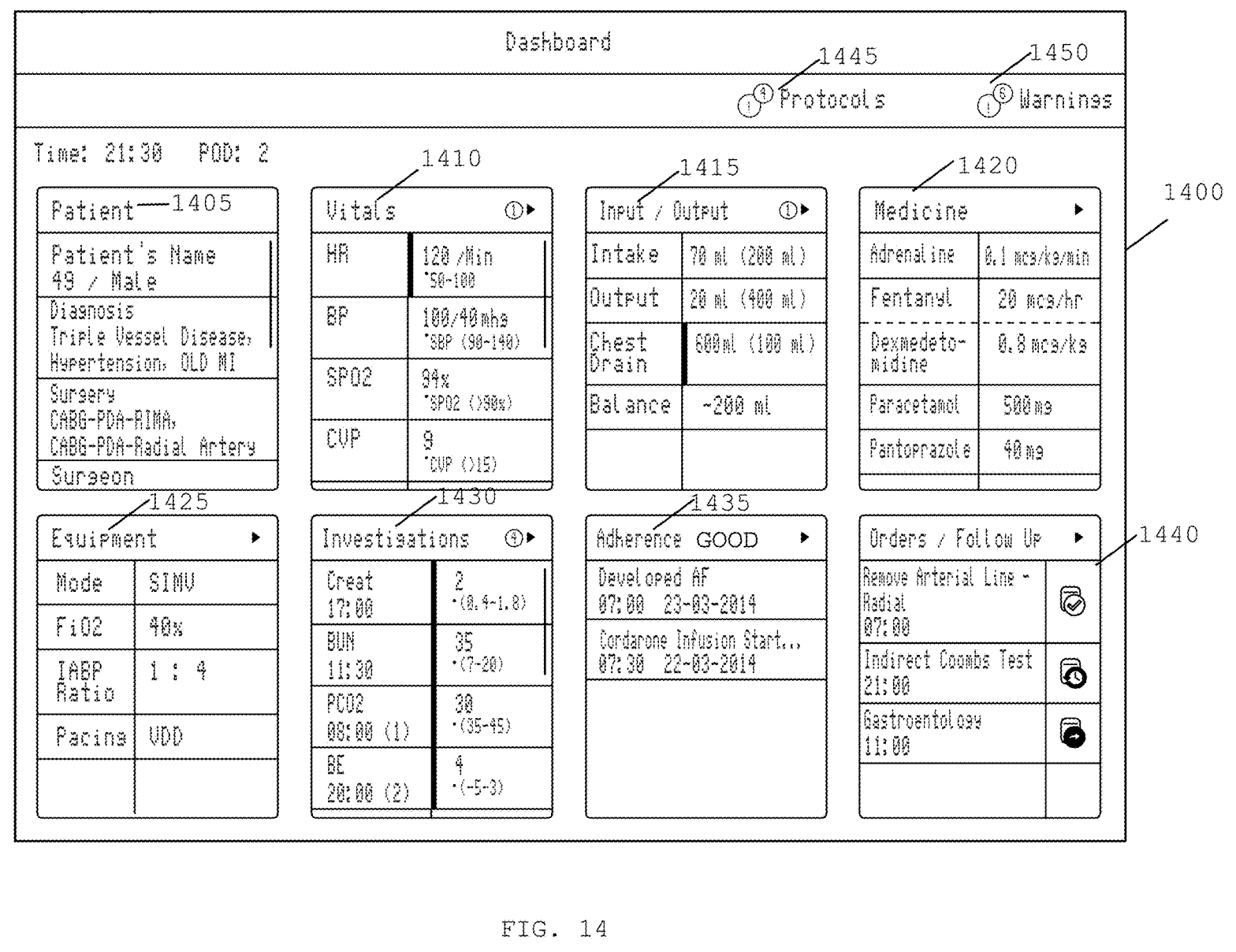

Dashboard
1445 Protocols
1450 Warnings
1400
Time: 21:30 POD: 2

Patient 1405
Patient's Name
49 / Male
Diagnosis
Triple Vessel Disease, Hypertension, OLD MI
Surgery
CABG-PDA-RIMA, CABG-PDA-Radial Artery
Surgeon Vitals 1410
HR 120 /Min *50-100
BP 100/40 mhg *SBP (90-140)
SPO2 94% *SPO2 (>90%)
CVP 9 *CVP (>15)

Input / Output 1415
Intake 70 ml (200 ml)
Output 20 ml (400 ml)
Chest Drain 600ml (100 ml)
Balance ~200 ml Medicine 1420
Adrenaline 0.1 mcg/kg/min
Fentanyl 20 mcg/hr
Dexmedeto-midine 0.8 mcg/kg
Paracetamol 500 mg
Pantoprazole 40 mg Equipment 1425
Mode SIMV
FiO2 40%
IABP Ratio 1 : 4
Pacing VDD Investigations 1430
Creat 17:00 2 ·(0.4-1.0)
BUN 11:30 35 ·(7-20)
PCO2 08:00 (1) 30 ·(35-45)
BE 20:00 (2) 4 ·(-5-3)

Adherence GOOD 1435
Developed AF
07:00 23-03-2014
Cordarone Infusion Start...
07:30 22-03-2014

Orders / Follow Up 1440
Remove Arterial Line - Radial
07:00
Indirect Coombs Test
21:00
Gastroentology
11:00

FIG. 14

SYSTEM AND METHOD FOR FACILITATING DELIVERY OF PATIENT-CARE

CROSS-REFERENCE TO RELATED APPLICATIONS

This application is a continuation of U.S. application Ser. No. 14/335,815, filed Jul. 18, 2014, which claims benefit of priority under 35 U.S.C. § 119(a) from Indian Patent Application Ser. No. 5563/CHE/2013, filed Dec. 3, 2013, the contents of which are incorporated by reference, and Indian Patent Application Ser. No. 5564/CHE/2013, filed Dec. 3, 2013, the contents of which are incorporated by reference.

BACKGROUND

1. Field

The present application generally relates to the field of clinical healthcare. More specifically, the present application relates to a system and method which facilitates delivery of patient-care with adherence to standard of care clinical protocols (sometimes referred to as “clinical pathways”; herein, the term “clinical protocols” is used collectively to refer to clinical pathways, clinical flows, clinical protocols, and equivalents thereof as would be understood by those skilled in the art) by physicians, nurses, care-givers or patients themselves.

2. Related Art

Software and its distribution in the healthcare industry involve one or more developers that develop and provide software to entities such as healthcare providers, physicians, nurses, etc. The entities are required to adhere to standard of care clinical protocols while providing patient-care using the software provided by such developers. Such adherence is usually prescribed for mitigating undesired circumstances and ensuring high quality patient outcomes across various patient populations.

The related art methods of ensuring adherence to standard of care clinical protocols involve manual chart entry and monitoring by healthcare professionals. Such methods and systems are typically prone to manual errors. Also, such a related art approach provides weak management and control over actual patient care and implementation of practices, and provides a lengthy feedback loop while involving various entities ranging from patients to various roles of healthcare professionals and software developers. Some available automated tools assist healthcare professionals in reducing manual errors. However, such tools typically focus on aspects of billing, administration and management, acquiring lab results, ordering tests, etc. However, none of these related art tools focus exclusively on timely actions for delivery of patient care at the point of care (e.g., hospital bedside, consultation room, at home, etc.).

Changes in technology have enabled enhanced synchronization between different entities involved in providing healthcare. Certain technology systems that exist today provide healthcare applications over multiple healthcare platforms. However, such related art systems are directed towards providing applications that are limited to post-care clinical decision analytics and billing. Further, such systems only facilitate hindsight adherence to standard of care clinical protocols through systematic review of system users after treatment has been completed, and do not provide real-time adherence to standard of care clinical protocols during treatment. Additionally, existing systems do not recalibrate treatment actions back to standard of care clinical protocols when treatment has diverged from such protocols.

Further, related art systems also do not adapt a simple and easy to use graphical user interface based on measured adherence or divergence from a standard of care clinical protocol so as to encourage adherence and/or drive treatment actions back toward the clinical protocol when divergence is detected.

Accordingly, there is an unmet need for systems or methods that may assist in providing patient-care by ensuring real-time adherence to standard of care clinical protocols, which may typically be evidence-based, established by entities such as, for example, hospitals, physicians and health authorities, as well as the patient, during treatment.

SUMMARY

One implementation of the present application may provide a computer-implemented method for facilitating delivery of patient-care, the method including monitoring, by a computing device, patient information indicative of a clinical condition, based on a clinical protocol that comprises patient-care instructions that must be completed within a time period, providing, by the computing device, the patient-care instructions to a user based on a result of the monitoring, determining, by the computing device, adherence to the clinical protocol based on a result of at least one of the providing patient care instructions and the patient information, and, for a determination that the clinical protocol has not been adhered to, providing a recommended action request that calibrates the patient care instructions in compliance with the clinical protocol.

Another implementation of the present application may further include specifying that at least one of the patient information be provided and the patient-care instructions be performed within the time period.

Another implementation of the present application may further include displaying to the user a count-down timer that is indicative of the time period.

Another implementation of the present application may further include at least one of taking one or more measurements of patient vital signs, obtaining one or more patient specimens and performing one or more laboratory tests on the one or more patient specimens, performing one or more radiological imaging tests on a patient or the one or more patient specimens, performing one or more physical diagnostic tests on the patient; and performing one or more medical procedures on the patient.

Another implementation of the present application may further include accessing, by the computing device, a hospital information system to retrieve additional patient information, correlating, by the computing device, the retrieved additional patient information with the monitored patient information based on the clinical protocol, and providing patient-care instructions by displaying a combination of the retrieved additional patient information, the monitored patient information, and diagnostic information based on the clinical protocol.

Another implementation of the present application may further include receiving role information of the user, requesting patient information based on the received role information of the user, and the patient-care instructions are provided based on the received role information of the user.

Another implementation of the present application may further the patient-care instructions being provided based on a determination of compliance with the standard of care protocol.

Another implementation of the present application may provide a non-transitory computer readable medium storing computer executable instructions for causing a computing device to perform the method including monitoring, by a computing device, patient information indicative of a clinical condition, based on a clinical protocol that comprises patient-care instructions that must be completed within a time period, providing, by the computing device, the patient-care instructions to a user based on a result of the monitoring, determining, by the computing device, adherence to the clinical protocol based on a result of at least one of the providing patient care instructions and the patient information, and for a determination that the clinical protocol has not been adhered to, providing a recommended action request that calibrates the patient care instructions in compliance with the clinical protocol.

Another implementation of the present application may further include monitoring patient information specifying that at least one of the patient information be provided and the patient-care instructions be performed within the time period.

Another implementation of the present application may further include displaying to the user a count-down timer that is indicative of the time period.

Another implementation of the present application may further include at least one of taking one or more measurements of patient vital signs, obtaining one or more patient specimens and performing one or more laboratory tests on the one or more patient specimens, performing one or more radiological imaging tests on a patient or the one or more patient specimens, performing one or more physical diagnostic tests on the patient, and performing one or more medical procedures on the patient.

Another implementation of the present application may further include accessing, by the computing device, a hospital information system to retrieve additional patient information, correlating, by the computing device, the retrieved additional patient information with the monitored patient information based on the clinical protocol, and wherein the providing the patient-care instructions comprises displaying a combination of the retrieved additional patient information, the monitored patient information, and diagnostic information based on the clinical protocol.

Another implementation of the present application may further include receiving role information of the user, monitoring patient information by requesting patient information based on the received role information of the user; and patient-care instructions are provided based on the received role information of the user.

Another implementation of the present application may further include the patient-care instructions being provided based on a determination of compliance with the standard of care protocol.

Another implementation of the present application may provide a computer-implemented method for distributing patient-care mobile applications to a user, the method including receiving, by a computing device, role information about the user, identifying a plurality of patient-care mobile applications targeted to the user based on the received role information, providing, by the computing device, summary information for the identified plurality of patient-care mobile applications to the user, receiving, by the computing device, selection information from the user identifying one of the plurality of patient-care mobile applications, and granting access to the identified one of the plurality of patient-care mobile application.

Another implementation of the present application may further include the role information including job information of the user within a healthcare organization, and the one or more of the patient-care mobile applications are identified based on the job information.

Another implementation of the present application may further include the job information including information indicative of the user's position as at least one of doctor, nurse, technician, administrator, patient, and payor.

Another implementation of the present application may further include the role information being department information identifying a department associated with the user within a healthcare organization, and one or more of the patient-care mobile applications may be identified based on the department information.

Another implementation of the present application may further include the department information including information indicative of the department associated with the user as at least one of: Cardiology, Internal Medicine, Obstetrics/Gynecology, Oncology, Radiology, Surgery, Pediatrics, Neonatology, Emergency Medicine, Nephrology, and Dermatology.

Another implementation of the present application may further include accessing, by the computing device, a hospital information system to determine diagnosis information associated with the user when the role information identifies the user as a patient, identifying the plurality of patient-care mobile applications based on the received role information by identifying the plurality of patient-care mobile applications based on the determined diagnosis information.

Another implementation of the present application may include a system for facilitating delivery of patient-care, the system may include a first computing device having a first storage and a first processor configured to perform monitoring patient information indicative of a clinical condition, based on a clinical protocol that comprises first patient-care instructions and second patient-care instructions that must be completed within a time period, providing the first patient-care instructions to a first user based on a result of the monitoring, determining adherence to the clinical protocol based on a result of at least one of the providing the first patient care instructions and the patient information; and for a determination that the clinical protocol has not been adhered to by the first user, providing a first recommended action request that calibrates the first patient care instructions in compliance with the clinical protocol, and a second computing device including a second storage and a second processor configured to perform monitoring patient information indicative of the clinical condition, based on the clinical protocol that comprises the first patient-care instructions and the second patient-care instructions that must be completed within a time period, providing the second patient-care instructions to a second user based on a result of the monitoring, determining adherence to the clinical protocol based on a result of at least one of the providing the second patient care instructions and the patient information, and for a determination that the clinical protocol has not been adhered to by the second user, providing a second recommended action request that calibrates the second patient care instructions in compliance with the clinical protocol, wherein the first computing device and the second computing device are each configured to provide an indication of adherence to the clinical protocol of the first user and the second user, respectively in a common indication format.

BRIEF DESCRIPTION OF DRAWINGS

The accompanying figures wherein like reference numerals refer to identical or functionally similar elements throughout the separate views and which together with the detailed description below are incorporated in and form part of the specification, serve to further illustrate various example implementations and to explain various principles and advantages all in accordance with the present application.

FIG. 4 illustrates a diagnostic chart used in the example protocol of FIG. 3.

FIG. 14 illustrates a user interface for facilitating patient-care with adherence to standard of care clinical protocols in accordance with a fourth example implementation of the present application.

Figure 1:
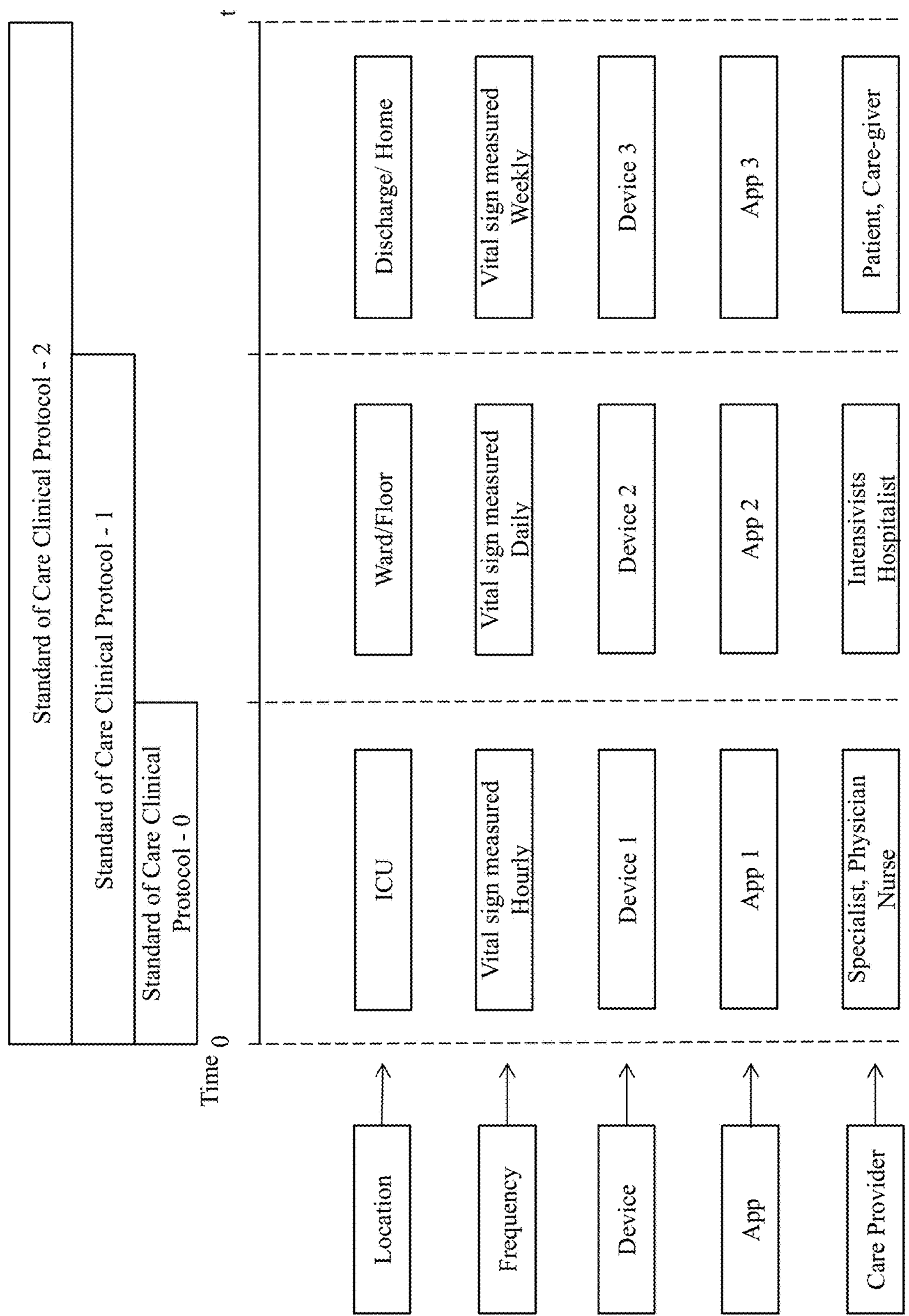
FIG. 1 illustrates an example standard of care clinical protocol that may be adhered to by an example implementation of the present application.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of example implementations of the present application.

DETAILED DESCRIPTION

Before describing in detail example implementations that are in accordance with the present application, it should be observed that the example implementations may include combinations of method steps and system components for facilitating patient care with adherence to standard of care clinical protocols. Accordingly, the method steps and system components have been represented where appropriate by conventional symbols in the drawings, showing only those specific details that are pertinent to understanding the example implementations of the present application so as not to obscure the disclosure with details that will be readily apparent to those of ordinary skill in the art having the benefit of the description herein.

In this document, the terms "comprises," "comprising," or any other variation thereof, are intended to cover a non-exclusive inclusion, such that a process, method, article, or apparatus that comprises a list of objects may include not only those objects but also include other objects not expressly listed or inherent to such process, method, article, or apparatus. An object proceeded by "comprises . . . a" does not, without more constraints, preclude the existence of additional identical objects in the process, method, article, or apparatus that comprises the object.

Various example implementations of the present application may provide a system for facilitating patient care with adherence to standard of care clinical protocols and a method for utilizing the system to provide patient care with adherence to the standard of care clinical protocols.

A "standard of care clinical protocol" may be best understood as a series of processes or treatment actions to be performed within a specified time or under certain circumstances, which may be derived from evidence-based healthcare practices, based on patient history and/or measured or perceived indicators of a patient's current status. Additionally, "clinical protocols" may be distinguished from "general protocols," based on "clinical protocols" being designed to be provided in response to a specific condition or situation for which clinical treatment is being provided by a trained healthcare provider. This distinction between clinical protocols and non-clinical, general protocols is well known in the art and for the sake of clarity, is not further discussed.

A "standard of care" example clinical protocol is illustrated in FIG. 1. As illustrated, the standard of care clinical protocol may be applied over a period of time, across a variety of locations, by a number of care providers. For example, along a timeline from 0 to t, the standard of care clinical protocol(s) is applied uniformly at multiple locations (such as the Intensive Care Unit (ICU), ward/floor, and at home after discharge) by different care providers (such as specialists, intensivists, nurses, hospitalists, etc.) including the patient. Some protocols may be applied in one location (e.g. Protocol —0 in FIG. 1 at the ICU), some protocols may be applied in two locations or more (e.g. Protocol —1 in FIG. 1 at the Ward/Floor and the ICU), and some protocols may be applied across all locations (e.g. Protocol —2 in FIG. 1 at the Ward/Floor and the ICU as well as the location of Discharge/Home).

The standard of care clinical protocol may dictate different actions or the same action being performed at different frequencies as time goes by and the patient's location and/or caregiver changes. For example, certain vital signs or blood chemistry measures might be required to be taken hourly when in the ICU, daily during the patient's stay in the general care ward/floor, and weekly when the patient has been discharged (e.g. to home, to an assisted care facility, to a hospice, etc.). To facilitate uniform adherence to the standard of care clinical protocol(s), example implementations of the present application may include one or more applications (App 1, App 2, App 3, etc.) running on one or more devices (Device 1, Device 2, Device 3, etc.) a series of steps to be performed at prescribed times and locations, in a given context. The one or more applications may include a Clinical Assessment and Recommendation Engine (CARE) to facilitate adherence to the standard of care clinical protocol. Additional details of the CARE are described further below.

Though the protocol is independent of provider, location, and physical environment, the clinical protocol is specific to the patient, and the condition of the patient. A single patient may be subject to one or more standard of care clinical protocols that are followed and tracked in parallel, overlapping, or in sequence, or any combination thereof. By providing the one or more applications (e.g., applications that include a CARE, such as a cardiac application that includes a CARE) running on one or more devices, adherence to all of the relevant protocols may be facilitated, which may in turn result in an overall reduction in the length of a patient's hospital stay, an improvement in the patient's condition/quality of treatment, and ultimately a reduction in costs by both the patient and the institutions providing the medical care.

Example implementations of the present application may provide a mechanism for adherence to the clinical protocol, and a feedback mechanism to recalibrate treatment by providers back to the clinical protocols, in cases of non-adherence. This adherence and recalibration is accomplished by one or more algorithms embedded in computerized applications that receive as input parameters (e.g., patient history, patient condition, patient treatment plan, location, patient vital signs, time, and other well-known indicators of a patient's status) relative to a clinical protocol. In some example implementations, the applications (e.g., applications that include a CARE) may be operated, controlled or used on one or more computerized devices such as tablets, smart phones, wearables, desktop, as well as centrally controlled, server-side or cloud implemented devices.

In some example implementations, the applications and their associated algorithms may be operated on a single device or maybe distributed across multiple devices. Control of the algorithm may residing in a server (e.g. cloud) or may be passed from device to device (e.g., client) over the course of the patient's treatment, for example, based on device capacity, signal strength, remoteness from an operator/administrator, convenience, level of security or other factors that should be well known to those skilled in the art.

The one or more devices may have a user interface (UI) with an appearance that varies based on one or more factors (such as a user's role within a care providing institution, patient's location within the hospital, past adherence or divergence from the protocol, or other factor that might be apparent to a person of ordinary skill in the art. For example, a nurse may be provided with a simplified UI (FIG. 11 discussed below, for example) with triggering conditions, diagnosis possibilities, requested inputs and timing conditions. Conversely, a doctor may be provided with a more detailed interface (FIG. 12 discussed below, for example). In other examples, the detailed interface of FIG. 12 may be provided when the protocol has been adhered to, and the simplified interface of FIG. 11 may be provided when the divergence from the protocol has been detected, in order to instruct the care provider what step or action should be taken next without any other distracting information in ensure compliance.

For example, but not by way of limitation, the clinical protocols may or may not cross physical locations, online computerized devices and users. Accordingly, the following illustrative examples are provided.

Figure 2:
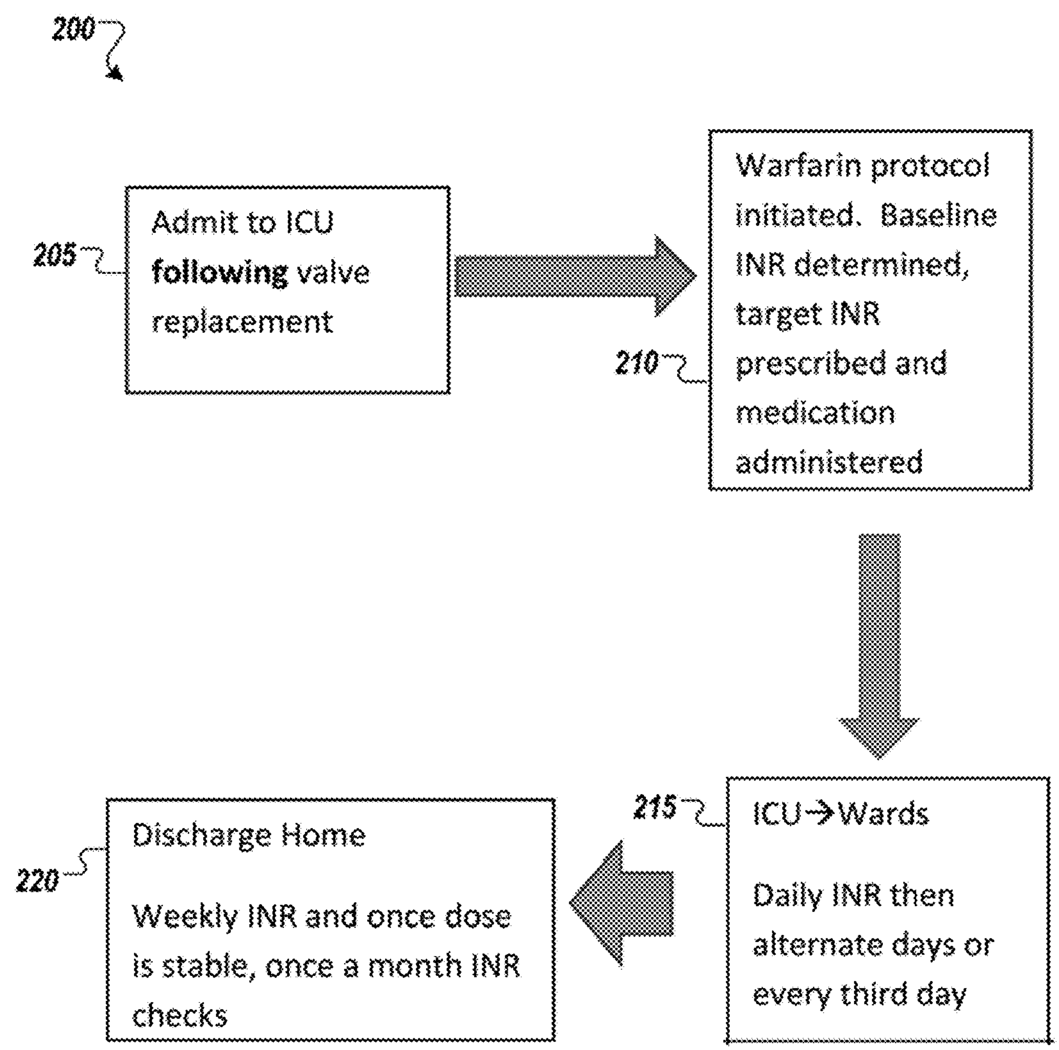
FIG. 2 illustrates an example protocol for determining Warfarin™ dosages according to a standard of care clinical protocol.

FIG. 2 illustrates an example protocol for the administration of Warfarin™ with consistent monitoring of the patient using one or more devices running one or more applications. Warfarin™ is a vitamin K antagonist that prevents blood from clotting. It is used to prevent thrombotic complications in patients who have mechanical prosthetic heart valves, have atrial fibrillation or other conditions that require anticoagulation. The dosage of warfarin is not constant across patients and must be closely monitored. If the dose is too high, spontaneous bleeding or excessive bleeding from minor trauma can occur. If the dose is too low, the blood can clot on the mechanical heart valve, leading to a blocked valve, a stroke, or both. However, Warfarin™ can be extremely effective in managing thrombotic conditions for post cardiac surgeries.

The Warfarin™ dose depends on the target INR (international normalized ratio) value, which is measured via a blood test to acquire Prothrombin levels in blood. Thereafter, a mathematical equation is used to calculate INR via control value to standardize the INR. Based on the test INR value, the Warfarin™ dosage may need to be adjusted.

As illustrated in FIG. 2, a typical scenario 200 may involve a patient being admitted to an ICU after valve replacement surgery 205. The patient who underwent a heart valve replacement with a mechanical valve prosthesis has been admitted to the ICU and has started receiving Warfarin™. In the early phase 210 after heart surgery, the Warfarin™ protocol is initiated. More specifically, a baseline INR is determined, a target INR value is prescribed, and the medication is administered. After Warfarin™ treatment is started 215, INR levels are monitored daily and doses adjusted. Then, the frequency of INR measurements decreases to alternate days, and then every third day as the patient transitions from the ICU to general care ward of the hospital. The day-to-day dose of Warfarin™ is determined based on the INR value. Based on the type of valve used in a patient, he/she may have to take warfarin for periods ranging from a few weeks to life. Therefore, the Warfarin™ dose has to be adjusted after the patient has been discharged. Immediately following discharge 220, the INR measurements may be measured weekly and then eventually once a month as the patient returns to normal activity.

During each of the stages illustrated in FIG. 2, INR values may be entered into a user interface of an app (e.g., online computerized application) running on one or more devices each time the patient receives an INR report, and with the built-in algorithm of the application, may provide a dosage suggestion. For example, an app on a tablet, PC, or wearable device may be used for entry within the hospital (e.g., in the ICU and/or in the general care ward). Once the patient has been discharged, another app on a smartphone or other device may be used, thus avoiding the human error of looking at an INR value that is not current, and in turn prescribing Warfarin™ dosage leading to undesirable consequences. Another issue may occur if a patient arrives at treatment with a report that shows a low INR from a week ago whereas the current INR is currently high. In such a situation, the person prescribing Warfarin™ may overlook the date on the report and increase the dose of Warfarin™, leading to overdose and bleeding complications. The algorithm may be configured to prevent a non-current INR value that is not current being entered prior to making a dosage recommendation.

Each value may have a guidance value as to what the target INR should be, and therefore what the corresponding Warfarin™ dosage should be. Warfarin™ dosage is dynamic, since it depends on diet (e.g., eating 100 grams of spinach can skew the INR value in blood test results due to spinach having a lot of vitamin K) and other factors, such as drug interactions. Other dynamic situations that can affect dosage measurements include a temporary liver dysfunction causing the INR values to shoot up which could lead to incorrect Warfarin™ dosage. Thus, Warfarin™ dosage requires close monitoring of patients. The patients typically receive literature on diet, medications that may negatively interact with Warfarin™ and how to record the date/time of food eaten, as well as recommend certain situations when INR should be retested again. Thus, the historical information of food habits prior to INR test is in some cases useful for physicians to have and may be collected by the applications during INR management.

By encouraging adherence to the clinical protocols, the applications running on the devices in the above discussed scenario may achieve better outcomes for the patient by ensuring accurate warfarin dosages by adhering to the Warfarin™ protocol.

Figure 3:
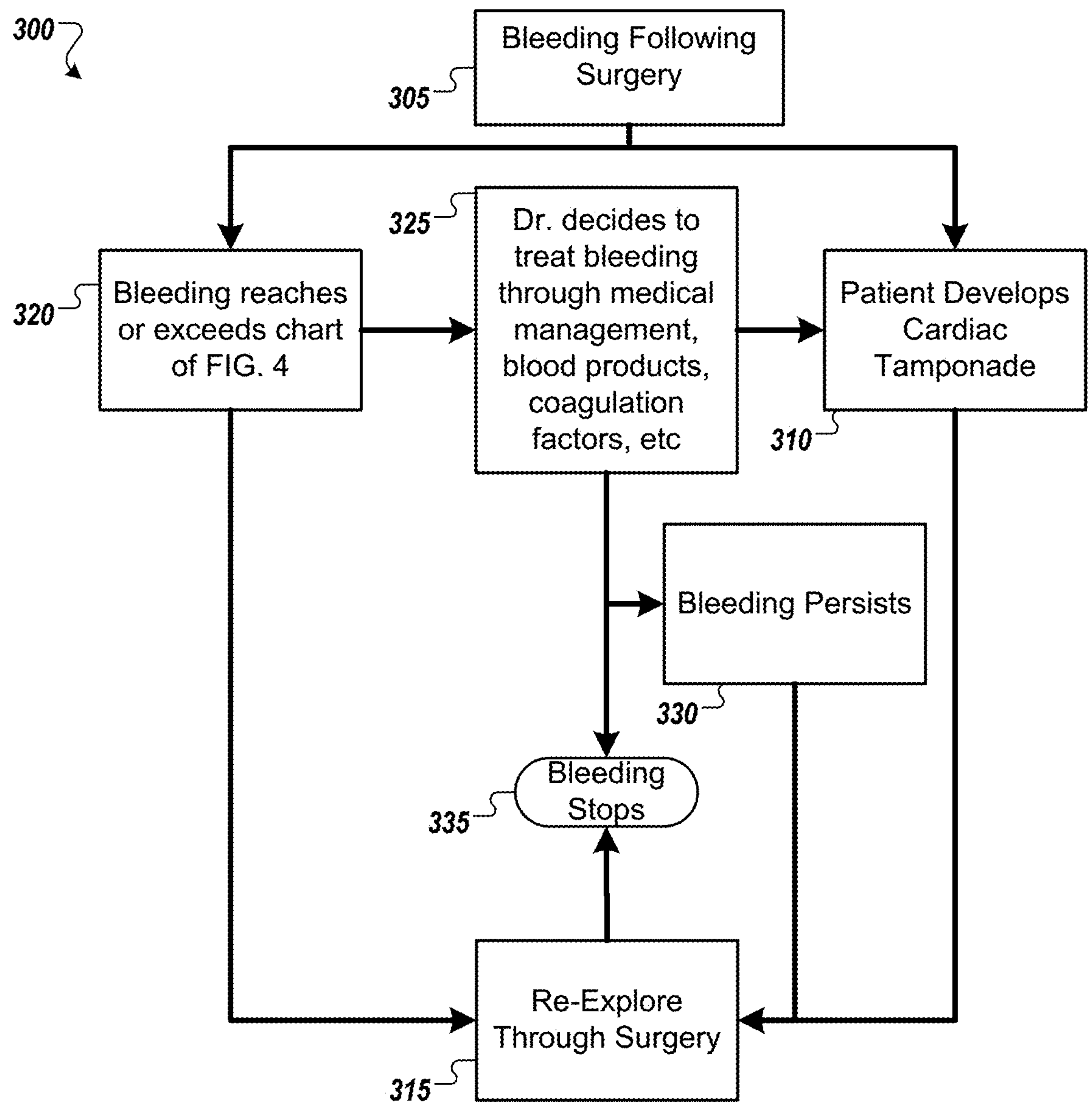
FIG. 3 illustrates an example protocol for determining response to post-surgical bleeding according to a standard of care clinical protocol.

Another common scenario illustrated using FIGS. 3 and 4, which may result in improved patient outcomes by using applications running on devices according the example implementations of the present application involves the monitoring of bleeding in a patient post-surgery (e.g., a pediatric patient). Bleeding can occur due to multiple factors such as the magnitude of the operation itself, the amount of dissected areas, inadequate surgical control of bleeding or inadequate optimization of blood coagulation following heparin reversal. During surgery, drains are placed in the pericardial and pleural cavities to drain the blood that is shed following closure of the chest. FIG. 3 illustrates a protocol 300 for monitoring bleeding and determining a course of action. Initially, bleeding of the patient is closely monitored in 305. If the blood does not drain and accumulates around the heart, it can lead to poor cardiac function and cardiac arrest from cardiac tamponade in 310, particularly if the pleura is intact and drains are non-functional. If there is evidence of cardiac tamponade, the patient must be re-operated upon quickly, blood clots evacuated and bleeding stopped in 315.

However in the absence of cardiac tamponade, the surgeon has discretion to take the patient back to the OR for examination. Some literature has recommended mathematical formulae based on the amount of bleeding, body weight and time since surgery to recommend a timely return to the OR for bleeding. FIG. 4 illustrates a diagnostic reference table that could be used to detect bleeding levels.

Using mathematical calculations, an algorithm in an application running on a device may suggest to the operating surgeon that the threshold for re-exploration has reached. For example, the bleeding levels can be monitored and recorded in the application, and based on the entered levels, the application may notify the doctor or surgeon when the bleeding reaches or exceeds the values provided in FIG. 4 in 320. In the protocol 300, the doctor may decide to take the patient back to surgery in 315 to evacuate blood clots and stop bleeding. Alternatively, in 325, based on the patient's condition from the perspective of coagulopathy and other medical conditions, the surgeon may decide to defer re-exploration and treat the coagulopathy with blood products or coagulation factors and wait longer to see if the bleeding stops 335. If these measures are ineffective he or she may still want to re-explore the patient. In the protocol 300, the doctor may elect to treat the bleeding through medical management using blood products, coagulation factors, etc., which may cause the bleeding to stop. However, if there is evidence of tamponade in 310, the patient needs to be re-operated upon quickly, blood clots evacuated and bleeding stopped in 315. Further, if the patient's bleeding does not respond to the medical treatment in 330, the doctor may decide to take the patient back to surgery in 315 to evacuate blood clots and stop bleeding even though no cardiac tamponade has developed.

By providing recommendations to the surgeon based on entered bleeding levels discussed in the above scenario, applications and algorithms according to example implementations of the present application can encourage adherence to the foregoing clinical protocol. By encouraging adherence to the clinical protocols, the applications running on the devices in the above discussed scenario may achieve better outcomes for the patient by ensuring accurate quicker reaction to increased bleeding levels.

Figure 5:
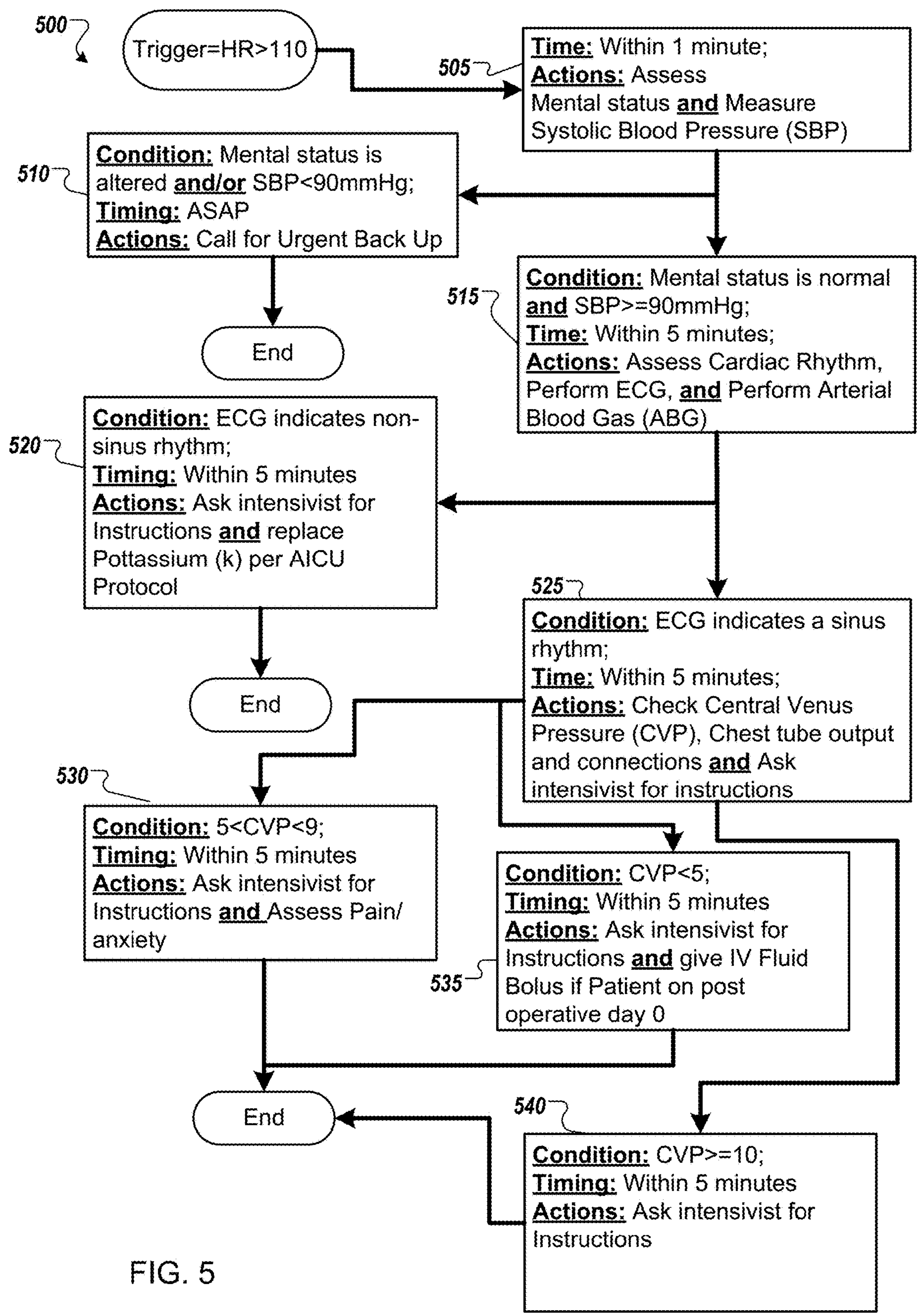
FIG. 5 illustrates an example protocol for treating Tachycardia according to a standard of care clinical protocol.

Another scenario that may demonstrate adherence to a clinical protocol is illustrated in a scenario where a patient in the cardiac ICU begins showing signs of tachycardia. FIG. 5 illustrates a standard of care protocol 500 performed in response to a patient presenting with heart rate (HR) greater than or equal to (>=) 100 beats per minute. According to an example implementation of the present application, at each stage in the protocol 500 a user enters information into an application running on a computing device using a UI, such as the UI illustrated in FIGS. 11 and 12 discussed in greater detail below. Further, in response to each entry a user is presented with an explanation of actions that should be taken and a timing condition within which the actions should be taken using a UI, such as the UI illustrated in FIG. 13.

Figure 11:
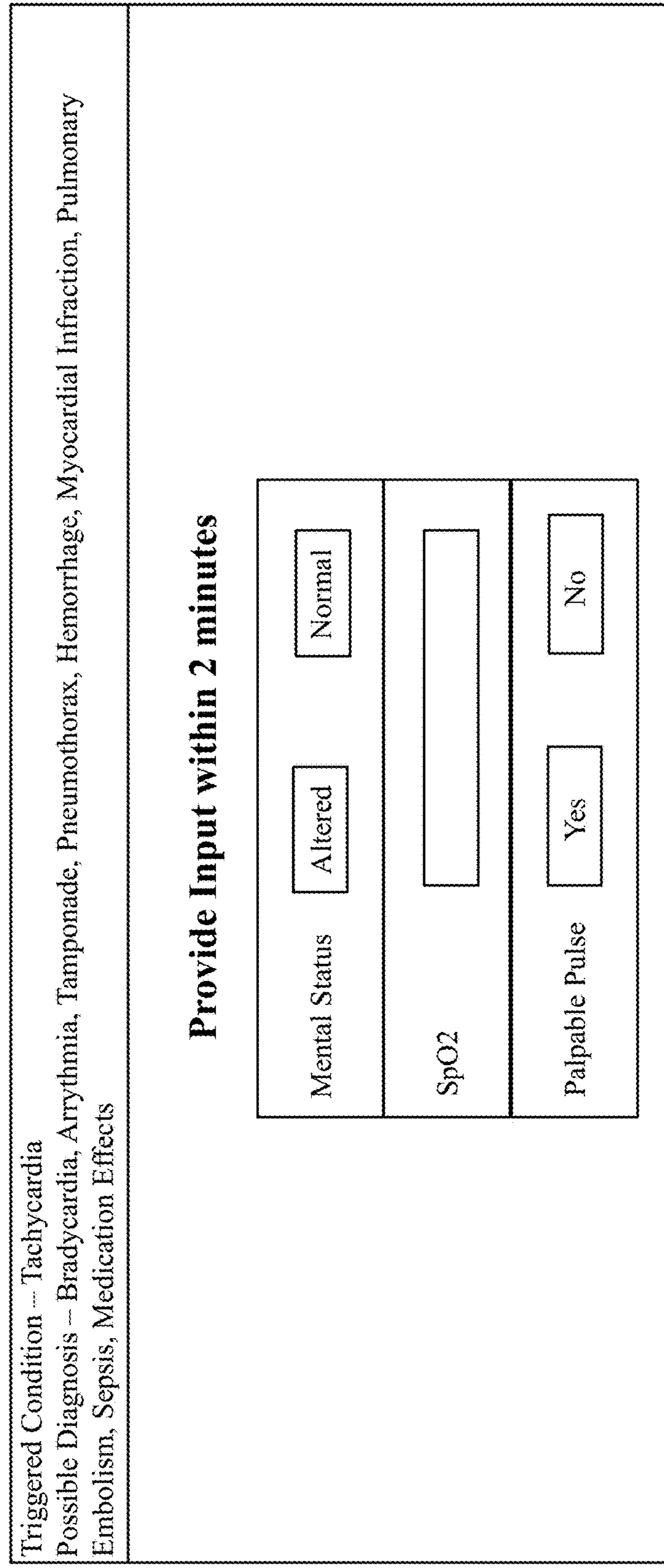
FIG. 11 illustrates a user interface for facilitating patient-care with adherence to standard of care clinical protocols in accordance with an example implementation of the present application.
Figure 12:
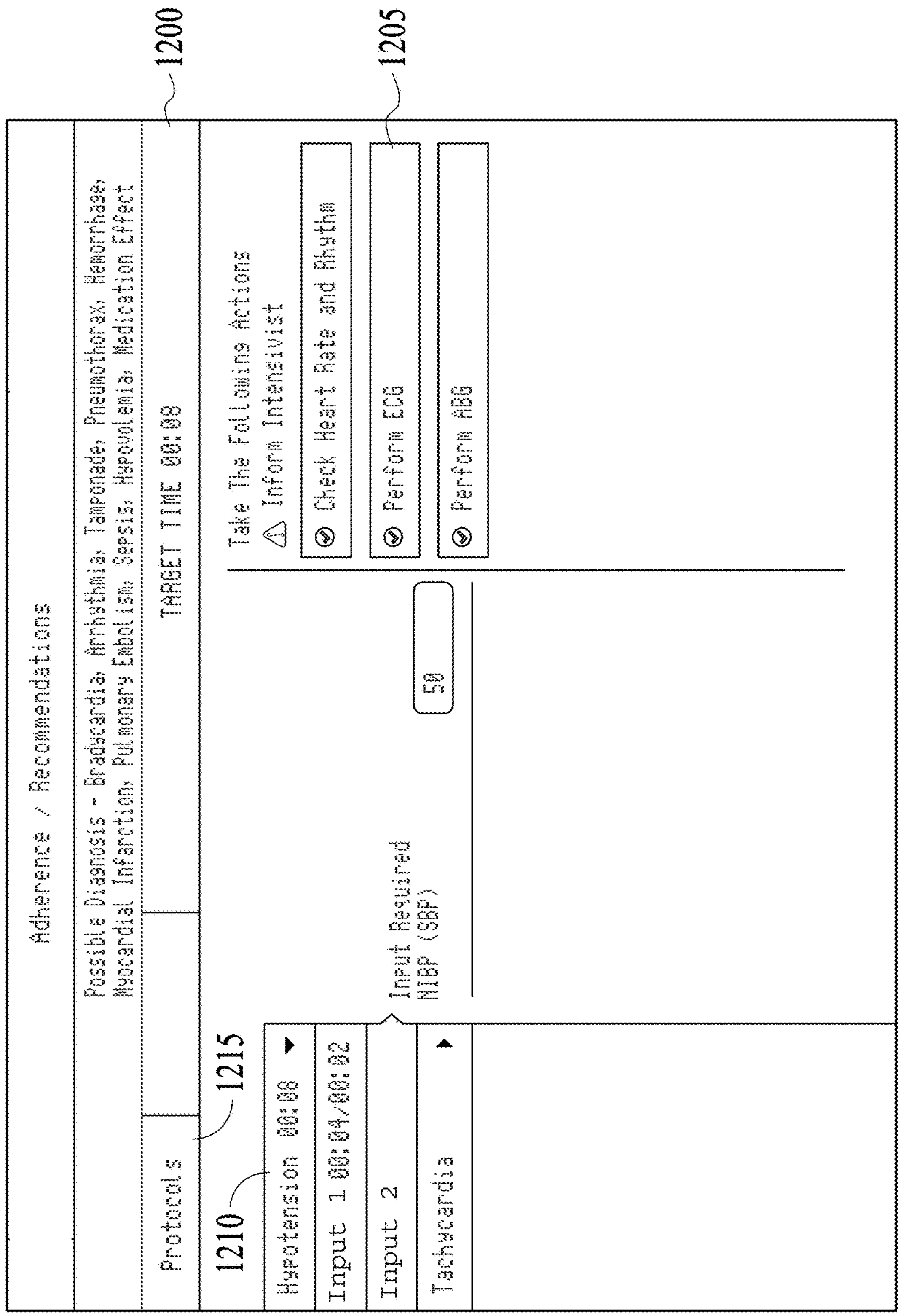
FIG. 12 illustrates a user interface for facilitating patient-care with adherence to standard of care clinical protocols in accordance with another example implementation of the present application.

For example, after the triggering condition (i.e. HR>=110), a UI such as that in FIGS. 11 and 12, may be provided requesting an assessment of patient mental status and measurement of Systolic Blood Pressure (SBP) within 1 minute in 505. Depending on the values entered, one of two instructions may be provided using another UI such as that in FIG. 13. In 510, if the patient's mental status is altered and/or the SBP is <90 mmHg, the user may be instructed to immediately call for urgent backup as the patient is in serious distress. Conversely, if the patient's mental status is normal and the SBP <90 mmHg, the user may be instructed to assess the patient's cardiac rhythm, perform an Electrocardiogram (ECG), and perform an arterial blood gas (ABG) within 5 minutes. In 520, if the ECG indicates a non-sinus rhythm, the user may be instructed to ask the intensivist for instructions and replace potassium (k) pursuant to Advanced ICU (AICU) protocols within 5 minutes. Conversely, in 525, if the ECG indicates a sinus rhythm, the user may be instructed to check Central Venus Pressure (CVP), chest tube output and connections, and ask the intensivist for instructions within 5 minutes. In 530, if the CVP is measured between 5 and 9, the user may be instructed to ask the intensivist for instructions and assess the pain and anxiety levels of the patient within 5 minutes. Conversely, in 535, if the CVP is measured below 5, the user may be instructed to ask the intensivist for instructions and administer an IV bolus of fluid within 5 minutes. Finally, in 540, if the CVP is greater than 10, the user may be instructed to ask the intensivist for instructions within 5 minutes.

Without the active cueing provided by an application driven by an algorithm designed to encourage adherence to the protocol, all the steps of the protocol must be remembered (e.g. memorized by a user) or manually reviewed on paper, and there is no centralized way to notify, display and force actions within the very time-sensitive periods illustrated in this protocol. Further, there would also be no integration across users by a monitoring engine that monitors the inputs by the users, an adherence engine that detects whether the protocol is being followed and a recommendation engine that provides the next step to be performed by the user with the UIs illustrated in FIGS. 11, 12, and 13. Conversely, actively cueing, and providing dynamic real-time feedback in the form of recommendations based on user input the one or more applications running on one or more devices, may increase adherence to all of the relevant protocols, resulting in an overall reduction in the length of a patient's hospital stay, an improvement in the patient's condition/quality of treatment, and a reduction in costs to both the patient and the institutions providing the medical care.

Figure 6:
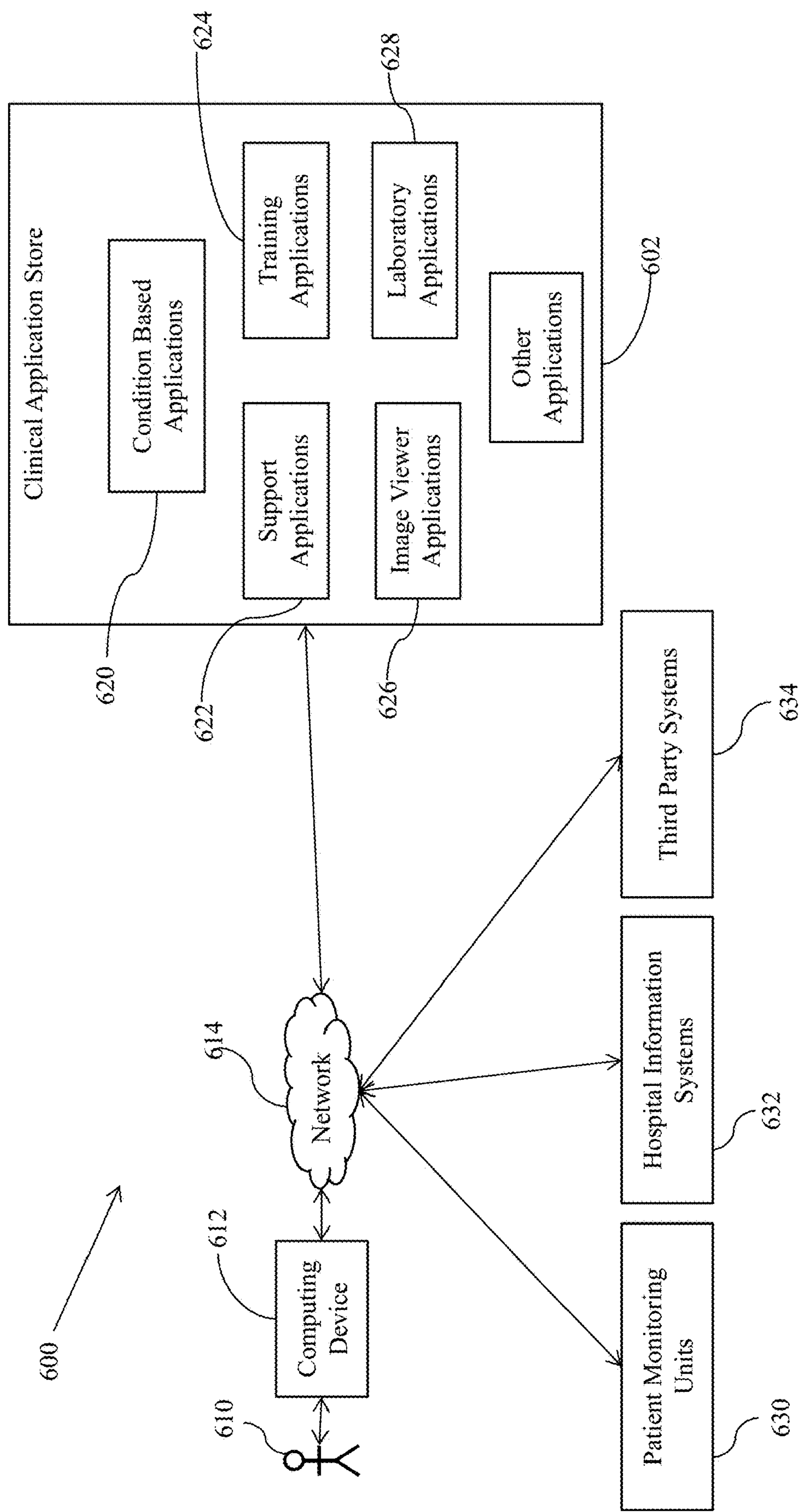
FIG. 6 illustrates a diagram of a system for facilitating patient care with adherence to standard of care clinical protocols in accordance with an example implementation of the present application.

FIG. 6 illustrates a diagram of a system 600 for facilitating delivery of patient care with adherence to standard of care clinical protocols in accordance with an example implementation of the present application. As illustrated, system 600 may include a clinical application store 602, a computing device 612, patient monitoring units 630, hospital information systems (HIS) 632 and third party systems 634.

Clinical application store 602 may be a network based application store similar to existing public application stores such as, but not limited to, the iTunes Appstore® of Apple®, the Play Store® of Google® and the Blackberry World® of Blackberry®. Further, clinical application store 602 can be hosted as one of, but not limited to, a cloud based private application store, a local area network based application store and a wireless area network based application store and other such implementations. Accordingly, clinical application store 602 may be configured to be accessible via a network 614 such as, but not limited to, cloud network, Local Area Network (LAN), Wireless Local Area Network (WLAN), Wireless Wide Area Network (WWAN), Wireless Metropolitan Area Network (WMAN), and Wide Area Network (WAN).

Clinical application store 602 may be configured to serve as a marketplace for a plurality of patient-care applications. Each of the plurality of patient-care applications may be one of, a mobile application and/or a computer application. Further, each application can be configured to work on an operating system such as, but not limited to, Windows®, Linux®, Android™, IOS™, and UNIX. In addition, each application can be configured to work according to one or more types of input such as, but not limited to, a keyboard input, a mouse input, a touch-based input, voice-based input and a gesture-based input. Moreover, each of the plurality of patient-care applications may be configured to be publicly and/or privately accessible. For example, a patient or a care giver of the patient can access the patient-care applications which are open to public. The patient-care applications that are private or proprietary applications can be accessed using authentication credentials by physicians, nurses and other staff on the hospital premises only.

Private or proprietary applications may be applications developed specifically for one or more entities including one or more of, but not limited to, hospitals, healthcare departments, healthcare providers, clinical laboratories and clinical experts. Accordingly, each of the private or proprietary applications may be configured such that general public does not have access to the application and only authorized personnel can access the application. Further, the configuration may allow access only after successful validation of access credentials provided by the authorized personnel. In addition, the configuration may allow access to privileged (e.g., confidential) data such as, but not limited to, patient diagnosis information and healthcare provider information.

As illustrated in FIG. 6, the plurality of patient-care applications may include condition based applications 620, symptom based applications, treatment based applications, diagnosis based applications, location based applications, population based applications, role based applications, specialty department based applications, remote monitoring based applications, actor based applications (payor, provider, etc.), messaging applications, third party developer applications, custom applications, support applications 622, training applications 624, image viewer applications 626 and laboratory applications 628. As may be apparent to a person of ordinary skill in the art, clinical application store 602 may include other types of clinical applications than the ones mentioned above such as, compliance/audit applications, meaningful use applications, and combinations thereof. As discussed in greater detail below, each application may be designed to drive compliance or adherence with the standard of care clinical protocols independent of what type of application (i.e. condition based application, support application, etc.) is involved.

Condition-based applications 620 may facilitate providing patient-care with adherence to standard of care clinical protocols. Accordingly, condition based applications 620 may include one or more of, cardiac applications, nephrology applications, respiratory applications, diabetes applications, arthritis applications and asthma applications. Further, each condition-based application 620 may be specific to one or more medical conditions. For example, a condition based application may be specific to one or more of, cardiac arrest, asthma, seizures, amputation, burns, diabetic emergencies, eye injuries, fractures, and poisoning or infection due to catheter injuries. In addition, each condition based applications 620 can be designed based on one or more standard of care clinical protocols associated with the one or more medical conditions.

For example, a condition-based application specific to cardiac arrest can be designed to drive adherence to a standard of care clinical protocol associated with cardiac arrest. Based on the standard of care clinical protocol, such an application may provide instructions or recommendations of treatment steps to be followed by a care-giver (i.e. nurse, doctor, etc.) or by the patient as well as timing conditions within which each treatment step must be performed. Further, each application may also be designed to receive input either automatically from automated sensors or patient vital sign monitoring devices (such as respiration monitors, cardiac monitors, blood pressure monitors, etc.) or manually entered by a caregiver or the patient. Based on the input, the application may provide updated instructions or recommendations of additional treatment steps to drive adherence to the treatment clinical protocol.

For example, if an input indicates that the clinical protocol is being followed by the caregiver or patient, the application may provide the next step in the clinical protocol. However, if an input indicates that the treatment has deviated from the clinical protocol, a different step or instruction may be provided to drive the treatment back toward the clinical protocol. In one example implementation, a standard of care clinical protocol may require that the patient perform a respiratory volume flow measurement 10 times per hour every hour and that the volume flow meets or exceeds a specific volume. In response to an input indicating that the required measurements are being taken as scheduled and are within the ranges specified by the clinical protocol, the application may recommend continuing the measurements for 7 days without consulting a doctor. Conversely, if the input indicates that the measurements are only being taken twice per hour and the respiratory volume flow measurements are repeatedly below the required volumes, the application may recommend that the patient immediately consult a respiratory specialist for additional treatment.

Likewise, a condition-based application specific to cardiac arrest and asthma can be based on standard of care clinical protocols for cardiac arrest and asthma, and may provide similar instructions and treatment step recommendations based on various inputs apparent to a person of ordinary skill in the art. Condition-based applications 620 need not be limited to the examples provided herein and numerous variations may be readily apparent to those ordinarily skilled in the art.

Support applications 622 may include applications which are specific to support personnel of healthcare providers. Support personnel can be from various departments such as, but not limited to, nursing, intensivist, administration, information technology, pharmacy, laboratories, mental health, physiotherapy and accounts. Each application may be tailored to the specific role of the provider for which the application is designed or targeted to ensure personnel within that role adhere to standard of care clinical protocols. For example, a support application 622 targeted to a nurse may provide recommendations of treatment steps that are to be performed by a nurse according to the established treatment clinical protocol, such as perform vital sign measurements, administer particular drugs, etc. Conversely, a support application targeted to an intensivist may provide different recommendations of treatments steps of procedures that are typically performed by the intensivist. Regardless of the user's role, the applications may each be tailored to drive real-time adherence to the standard of care clinical protocol by the user by providing recommendations of treatment steps in response to inputs indicating compliance or deviation from the clinical protocol.

Training applications 624 are designed to facilitate training of one or more healthcare professionals such as, nurses, pharmacists and physicians. Each application of training applications 624 may be configured to enable a simulation of a real-time event such as, but not limited to, a medical emergency. For example, a training application specific to an emergent asthma patient may facilitate training of a nurse by providing an interface to enter details of a medical condition of a patient. The training application may provide patient-care related instructions to the nurse based on the entered details. The instructions may be patient-care actions which the nurse is required to perform for the emergent asthma patient.

Image viewer applications 626 may be applications designed to enable one or more healthcare professionals to virtually access medical imaging data of one or more patients. The medical imaging data can include one or more of, digital X-ray, Magnetic Resonance Imaging (MRI) data, Computer Tomography (CT) scan, ultrasound and fluoroscopy, etc.

Laboratory applications 628 enable one or more healthcare professionals to view laboratory data stored in one or more clinical trial databases. The laboratory data can include one or more of, blood test data, urine culture data, and tissue test data, but is not limited thereto.

The plurality of patient-care applications need not be limited to the examples illustrated in FIG. 6 and described above, and numerous variations in the plurality of patient-care applications would be readily apparent to those ordinarily skilled in the art.

The plurality of patient-care applications may be categorized into a plurality of levels. For example, the plurality of patient-care application may be classified based on requirements of one or more of, a network of hospitals/clinics, a hospital/clinic/nursing-home/hospice-care, a building, a floor, a department, a group of beds, a group of rooms, a bed and a room. The degree of security, data protection and access control can be different for different levels. For example, patient-care applications specific to one building of a hospital may not be accessible to healthcare professionals from another building of the same hospital. The patient-care applications may be tailored to provide recommendations of treatment steps specific to the level with which it is associated. For example, an application may provide recommendations and request inputs specific to a particular department of the hospital (e.g. cardiology, radiology, pharmacy, etc.). Regardless of the level or department, the applications may each be tailored to drive real-time adherence to the standard of care clinical protocol within the department by providing recommendations of treatment steps in response to inputs indicating compliance or deviation from the clinical protocol.

A user 610 can access one or more of the plurality of patient-care applications from clinical application store 602 to provide patient-care in accordance with standard of care clinical protocols. A user 610 accessing clinical applications store 602 can be any one of, a doctor, a physician, a nurse, a care giver, a patient, a practitioner, a lab assistant, a healthcare professional, a clinical expert, a clinical specialist, a software or application developer, an administrator or any other user that may be apparent to a person of ordinary skill in the art. For example, a software developer can access clinical application store 602 for developing and/or improving the design of one or more of the plurality of patient-care applications.

User 610 can access one or more of the plurality of patient-care applications using a computing device 612. Computing device 612 can be one of, but not limited to, a computer, a laptop, a phone, a tablet, a handheld device, a bed-side device, a wearable device (e.g., a smart-watch), a television, and a portal digital device. Each application may be tailored to provide treatment recommendations and requesting inputs specific to the capabilities of the computing device. For example, an application running on a wearable device with incorporated sensors may monitor patient vitals or movements using the sensors. As another example, an application running on a phone, laptop, or tablet connected to the internet or mobile cellular networks may send an automatic email, or call a specialist when necessary based on the received input and the standard of care clinical protocol. For example, if the respiratory volume measurements discussed above indicate that a specialist is needed, the application may call or email a designated physician. Regardless of the type of computing device being used, the application may be tailored to drive real-time adherence with the standard of care clinical protocol by providing recommendations of treatment steps in response to inputs indicating compliance or deviation from the clinical protocol.

Computing device 612 includes a storage and processor configured to facilitate patient-care with adherence to standard of care clinical protocols. Computing device 612 can be configured to include an application that contains CARE. The application that contains CARE can be installed on a computing device 612 to facilitate the recommending, downloading, installing and using other patient-care applications based on different clinical protocols from a clinical application store 602. For example, computing device 612 may be a computer in an X-ray department configured to facilitate downloading, installing and/or use of X-ray related applications from clinical application store 602. Similarly, computing device 612 may be a neurologist's tablet device configured to facilitate downloading, installing and/or use of neurology related applications. Taking another example, computing device 612 may be a patient's smartphone configured to facilitate downloading, installing and/or use of publically accessible patient-care applications.

Figure 7:
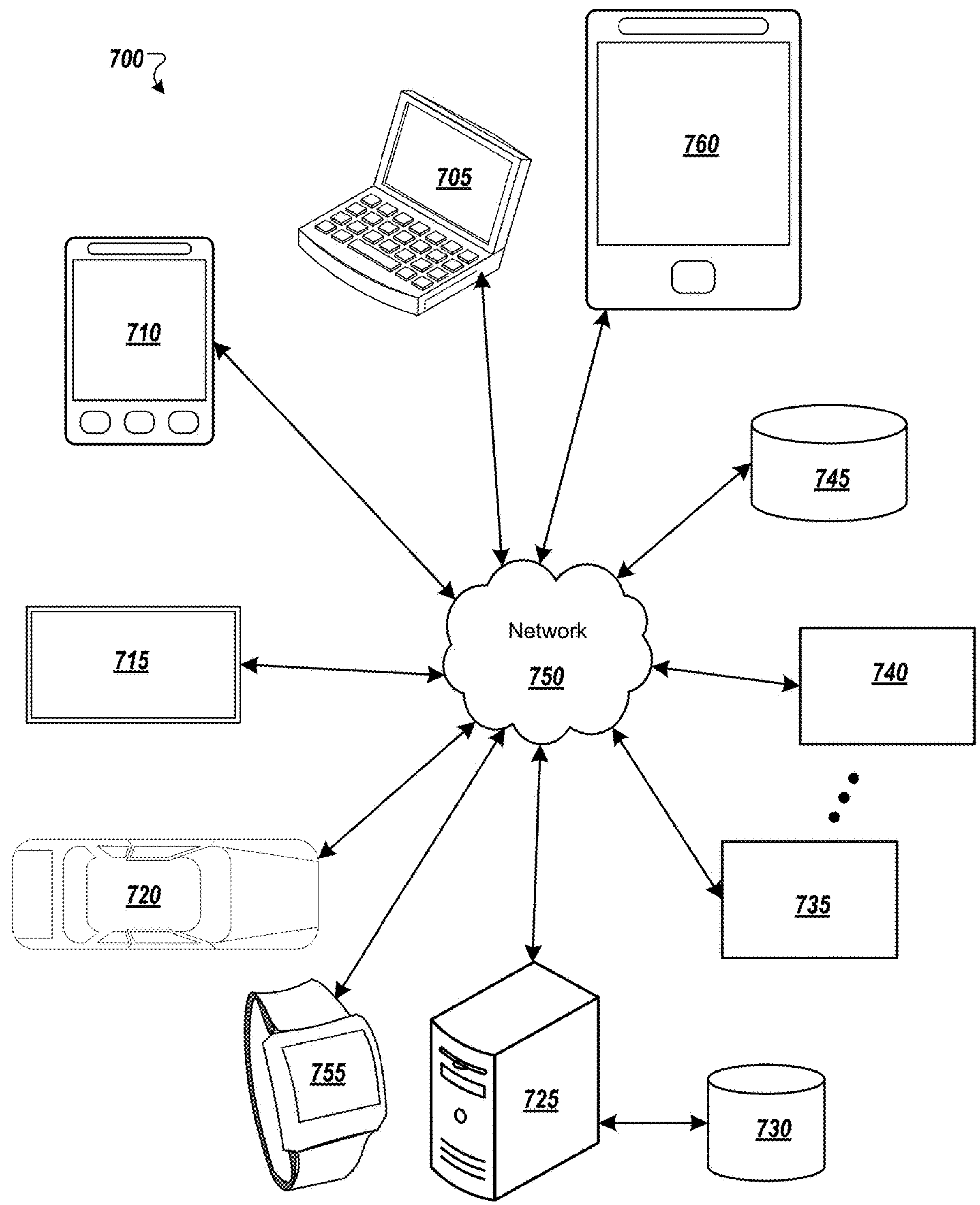
FIG. 7 shows an example environment suitable for some example implementations.

FIG. 7 shows an example environment suitable for some example implementations. Environment 700 includes devices 705-745, and each is communicatively connected to at least one other device via, for example, network 760 (e.g., by wired and/or wireless connections). Some devices may be communicatively connected to one or more storage devices 730 and 745.

An example of one or more devices 705-745 may be computing device 805 described below in FIG. 8. Devices 705-745 may include, but are not limited to, a computer 705 (e.g., a laptop computing device), a mobile device 710 (e.g., smartphone or tablet), a television 715, a device associated with a vehicle 720, a server computer 725, computing devices 735-740, storage devices 730 and 745. Computing devices 760 illustrate an implementation as a tablet device. Further computing device 755 also includes wearable computing devices (e.g. a smartwatch). In particular, the use of wearable computing 755 devices may provide additional functionality over tablets, phones, and other computing devices by directly monitoring patient vitals and other information by being attached directly to the patient. Additionally, the wearable may also facilitate additional usage by care providers (such as doctors, nurses, etc.) by freeing one or more limbs for use in treatment, while still facilitating access to the computing device wearable. For example, a nurse wearing a watch-like wearable computing device may be able to review instructions, recommendations by looking at their wrist will still having one hand free to take patient vitals.

Figure 8:
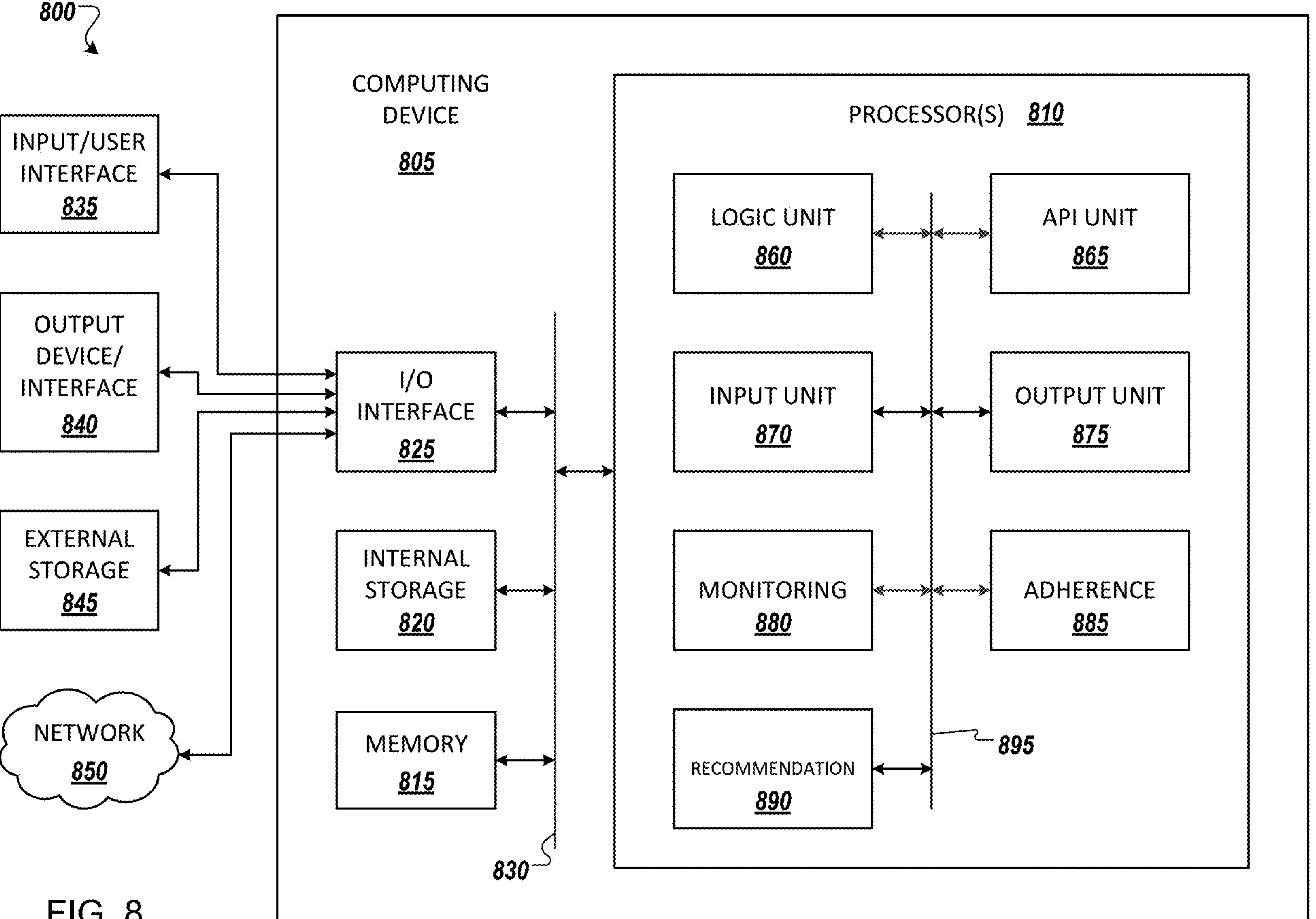
FIG. 8 shows an example computing environment with an example computing device suitable for use in some example implementations.

FIG. 8 shows an example computing environment with an example computing device suitable for use in some example implementations. Computing device 805 in computing environment 800 can include one or more processing units, cores, or processors 810, memory 815 (e.g., RAM, ROM, and/or the like), internal storage 820 (e.g., magnetic, optical, solid state storage, and/or organic), and/or I/O interface 825, any of which can be coupled on a communication mechanism or bus 830 for communicating information or embedded in the computing device 605.

Computing device 805 can be communicatively coupled to input/user interface 835 and output device/interface 840. Either one or both of input/user interface 835 and output device/interface 840 can be a wired or wireless interface and can be detachable. Input/user interface 835 may include any device, component, sensor, or interface, physical or virtual, that can be used to provide input (e.g., voice, buttons, touch-screen interface, keyboard, a pointing/cursor control, microphone, camera, braille, motion sensor, optical reader, and/or the like). Output device/interface 840 may include a display, television, monitor, printer, speaker, braille, or the like. In some example implementations, input/user interface 835 and output device/interface 840 can be embedded with or physically coupled to the computing device 805. In other example implementations, other computing devices may function as or provide the functions of input/user interface 835 and output device/interface 840 for a computing device 605.

Examples of computing device 805 may include, but are not limited to, highly mobile devices (e.g., smartphones, devices in vehicles and other machines, devices carried by humans and animals, and the like), mobile devices (e.g., tablets, notebooks, laptops, personal computers, portable televisions, radios, and the like), and devices not designed for mobility (e.g., desktop computers, other computers, information kiosks, televisions with one or more processors embedded therein and/or coupled thereto, radios, and the like).

Computing device 805 can be communicatively coupled (e.g., via I/O interface 825) to external storage 845 and network 850 for communicating with any number of networked components, devices, and systems, including one or more computing devices of the same or different configuration. I/O interface 825 can include, but is not limited to, wired and/or wireless interfaces using any communication or I/O protocols or standards (e.g., Ethernet, 802.11x, Universal System Bus, WiMax, modem, a cellular network protocol, and the like) for communicating information to and/or from at least all the connected components, devices, and network in computing environment 800. Network 850 can be any network or combination of networks.

Computing device 805 can use and/or communicate using computer-usable or computer-readable media, including transitory media and non-transitory media. Transitory media include transmission media (e.g., metal cables, fiber optics), signals, carrier waves, and the like. Non-transitory media include magnetic media (e.g., disks and tapes), optical media (e.g., CD ROM, digital video disks, Blu-ray disks), solid state media (e.g., RAM, ROM, flash memory, solid-state storage), and other non-volatile storage or memory.

Computing device 805 can be used to implement techniques, methods, applications, processes, or computer-executable instructions in some example computing environments. Computer-executable instructions can be retrieved from transitory media, and stored on and retrieved from non-transitory media. The executable instructions can originate from one or more of any programming, scripting, and machine languages (e.g., C, C++, C#, Java, Visual Basic, Python, Perl, JavaScript, and others).

Processor(s) 810 can execute under any operating system (OS) (not shown), in a native or virtual environment. One or more applications can be deployed that include logic unit 860, application programming interface (API) unit 865, input unit 870, output unit 875, monitoring unit 880, adherence unit 885, recommendation unit 890, and inter-unit communication mechanism 895 for the different units to communicate with each other, with the OS, and with other applications (not shown). For example, monitoring unit 880, adherence unit 885, and recommendation unit 890 may implement one or more of the processes disclosed herein. The described units and elements can be varied in design, function, configuration, or implementation and are not limited to the descriptions provided.

In some example implementations, when information or an execution instruction is received by API unit 865, it may be communicated to one or more other units (e.g., logic unit 860, input unit 870, output unit 875, monitoring unit 880, adherence unit 885, and recommendation unit 890). As explained above, the monitoring unit 880 may be implemented to receive information about the patient, or conditions of the patient; when the protocol is not being followed, the adherence unit 885 may take further steps as explained above, including on one or more devices and via one or more user interfaces; the recommendation unit 890 may recommend actions to be taken, to correct the situation and recover to the protocol.

In some instances, logic unit 860 may be configured to control the information flow among the units and direct the services provided by API unit 865, input unit 870, output unit 875, monitoring unit 880, adherence unit 885, and recommendation unit 890 in some example implementations described above. For example, the flow of one or more processes or implementations may be controlled by logic unit 860 alone or in conjunction with API unit 865.

In order to facilitate patient-care with adherence to standard of care clinical protocols, the computing device 612 may be configured to receive role information of a user 610. The role information of user 610 can include one or more of, but not limited to, job information, and department information. The job information provides details regarding user 610's position within a healthcare organization. The job information may identify the user 610's position as one or more of, but not limited to, a doctor, a nurse, a technician, an administrator, a patient and a payor. The department information provides details regarding a department associated with the user 610 within a healthcare organization. The department information can identify the department associated with user 610 as one or more of, but not limited to, Cardiology, Internal Medicine, OB/GYN, Oncology, Radiology, dermatology, neonatology, Surgery, and Pediatrics.

The computing device 612 may be further configured to identify a plurality of patient-care applications targeted to user 610 based on the received role information. Further, one or more of the patient-care applications may be identified based on the job information. For instance, if user 610 is identified as a cardiologist, then computing device 612 may identify a plurality of cardiac applications for user 610. In addition, one or more of the patient-care applications can be identified based on the department information. For instance, if user 610 is identified as a cardiologist who is associated with a surgery department of a hospital, then computing device 612 can identify a plurality of cardiac surgery related applications for user 610.

Computing device 612 may also be configured to access a Hospital Information System (HIS) 634 to determine diagnosis information associated with user 610, when the role information identifies the user as a patient. The determined diagnosis information can also be used for identifying the plurality of patient-care applications. For example, if user 610 is diagnosed with a bronchial infection, then a plurality of bronchial infection related applications can be identified for user 610.

Subsequently the computing device 612 may provide summary information for the identified plurality of patient-care applications to user 610. The summary information can be displayed as a list on the computing device 612. Further, a graphical icon corresponding to each of the identified plurality of patient-care applications can be displayed. Computing device 612 also provides an option to select one or more of the identified plurality of patient-care applications to user 610 via computing device 612. For example, a selection label may be associated with each of the identified patient-care application presented in the summary information. Accordingly, upon receiving the summary information, user 610 can select one or more of the identified plurality of patient-care applications by using the selection labels. Computing device 612 accordingly may enable access to the selected patient-care applications. This may encompass downloading, installing and utilizing the selected applications on a computing device 612. Further, an application including CARE that runs on a computing device 612 may be used to achieve the desired configuration.

Optionally, computing device 612 can be configured to transmit delivery information to HIS 634. The delivery information may identify that the selected patient-care applications have been delivered to the user.

Once the computing device 612 is configured with the desired patient-care applications, the CARE can be used to provide one or more user interfaces (UIs) which may enable the user 610 to control the manner of interaction and utilization of the desired patient-care applications accessed from clinical application store 602 via computing device 612. Thus, computing device 612 utilize one or more applications having a CARE to facilitate exchange of information with user 610 by enabling user 610 to provide one or more inputs. The CARE accordingly provides an output based on analysis of the input data, wherein the output can include recommendations for user 610. The output information provided by CARE can include, but is not limited to, text, audio, video, images and vibration. Accordingly, user 610 can perform the actions provided as recommendations. For example, the recommendations can be to take a reading from an electrocardiograph or to call a physician. Subsequently, the CARE automatically sends instructions based on analysis of the input data to one or more of, but not limited to, a computing device 612, a new department of users, and an on-line private/public human/social network of users and an on-line private/public forum of users. For example, the CARE may instruct the computing device 612 to request an X-ray procedure for a patient.

The CARE may recommend the user 610 to perform certain actions related to patient-care in a stepwise manner based on a standard treatment clinical protocol, wherein user 610 can provide an input regarding status of each step. User 610 utilizes one or more buttons displayed on UI of computing device 612 to indicate if the recommended action is completed or rejected. For example, the first step of recommendation can be to take a reading from an automatic blood pressure measuring device. Once the reading is taken, a nurse provides input to computing device 612 as the first step is performed which in turn displays that the systolic pressure is above 120, so alert/call a physician. In accordance with the example, the computing device 612 recommends the attended physician to perform necessary patient-care actions to treat the patient. Thereafter, the physician performs the recommended actions and provides input to the computing device 612 as a confirmation of action performed.

For example, in an advanced cardiac support situation, the computing device 612 may recommend that the doctor perform one or more treatment steps based on a standard of care clinical protocol in a particular amount of time by displaying instructions on the display screen, by voice instructions, or other visual or audio cue (such as voice instructions, tones, diagrams, lights. etc.). Additionally, a countdown time may also be provided while the recommendations are being provided. Further, additional alarms, tones, lights, and other additional cues may be provided during the countdown to encourage the doctor to perform the recommend treatment step or steps within the required time. Based on an input received from the doctor the computing device 612 may determine if the standard of care clinical protocol has been adhered to or has been deviated from. Based on this determination, the computing device 612 may include a recommendation engine to provide additional recommendations based on predetermined algorithms. For example, if the computing device 612 determines that the clinical protocol has been followed and the treatment steps have been performed as required, the next step in the clinical protocol may be recommended. However, if the computing device 612 determines that the clinical protocol has not been followed; different treatment steps may be recommended to drive the treatment back to the clinical protocol.

Consider another example, where the computing device 612 may alert a pharmacist keeping track of availability of specific medicines, which may be scarce or difficult to procure. The computing device 612 after analyzing one or more medical conditions of a patient may determine that the patient may require a specific medicine in the near future. Accordingly, the computing device 612 may alert a pharmacist to maintain a stock of, or to commence procurement of, the specific medicine. Depending on the stock availability or procurement status, an input may be provided by the pharmacist to the computing device 612 via network 614 confirming the availability of the specific medicine or sending an update regarding non-availability of the specific medicine.

The CARE can also be used to facilitate training of the user 610 to adhere to one or more care clinical protocols associated with one or more medical conditions. For example, the CARE can be configured to enable a simulation of a real-time event, such as, but not limited to, a medical emergency.

The CARE also may record inputs and actions performed by user 610 while facilitating patient-care. The CARE accordingly may enable the user 610 to view the recorded inputs and actions to be used for auditing and compliance purposes. For example, the recorded information can be used to check if a nurse performed actions as per a standard of care clinical protocol in response to a medical condition. Taking another example, the data of a healthcare department or multiple healthcare departments can be audited to check for compliance. Similarly, the data corresponding to an entire hospital can be reviewed for audit and compliance purposes.

Computing device 612 can also be integrated with one or more systems such as, but not limited to, patient monitoring units 630, hospital information systems (HIS) 632 and third party systems 634. Patient monitoring units 630 may include, but are not limited to, an intra-aortic balloon pump (IABP), an arterial blood gas (ABG), a ventilator and a bed-side monitor. The HIS 632 disclosed herein can include one or more systems such as, but not limited to, an Epic® system, a Cerner® system and a Hinai® system. Third party systems 634 may include, but are not limited to, system owned or controlled by payors, hospitals, clinics, primary care centers, diagnostic laboratories, pharmacies, nursing homes, physicians, nurses and other healthcare service delivery points. Optionally, clinical application store 602 can be integrated with the one or more systems including, but not limited to, patient monitoring units 630, HIS 632 and third party systems 634. Accordingly, computing device 612 can access one or more of patient monitoring units 630, HIS 632 and third party systems 634 via the clinical application store 602.

The integration between the one or more systems, one or more computing devices 612 and the clinical application store 602 can be performed to enable a plurality of applications. For instance, the integration can be performed to enable exchange of information between the computing device 612 and the patient monitoring units 630. For example, a blood pressure monitor can be integrated with the computing device 612 to feed blood pressure data to the computing device 612. In accordance with this example, computing device 612 may also trigger a blood pressure reading. Similarly, clinical application store 602 can be integrated with HIS 632 to enable access to data stored in the HIS 632. Likewise, third party systems 634 can be integrated to enable access to information related to treatment clinical protocols.

The system 600 need not be limited to one computing device such as 612 and one user such as user 610 as illustrated in FIG. 6. Multiple devices and users may simultaneously utilize the system 600. Further, system 600 can include additional components and/or integrations with external systems or between components than the ones mentioned above. Further, each component can have other functions than the ones listed above. Such variations would be readily apparent to those ordinarily skilled in the art.

System 600 can be used for multiple applications. For example, system 600 can be used for ensuring compliance with standard of care clinical protocols, accessing/developing patient-care applications, data gathering and analysis, viewing trends and so forth.

In one exemplary application, system 600 is configured to enable one or more application developers to develop patient-care applications using the clinical application store 602. In addition, system 600 may be configured to enable the one or more application developers to upload the plurality of patient-care applications to the clinical application store 602 for the one or more healthcare providers. Additionally, system 600 may be configured to enable the one or more application developers to access one or more of the HIS 632 and the third party systems 634 via clinical application store 602. The one or more application developers can use the HIS 632 and/or third party systems 634 to improve the design of the plurality of patient-care applications. Further, system 600 is configured to provide the application developers with software development toolkits (SDKs), User Interface (UI) template/patterns, style/coding guidelines, application programming interfaces (APIs), clinical experts, social network, community forums, source-code templates, release notes and access to clinical tests and clinical verification sites for developing the plurality of patient-care applications. The application developers may create a new clinical application faster and with ease using such information. System 600 is also configured to enable the one or more application developers to update the patient-care applications if there is a need to improve patient-care systems of the one or more healthcare providers.

In another exemplary application, system 600 is configured to enable one or more payors to access one or more of the plurality of patient-care applications in clinical application store 602 to determine the amount to be paid to one or more healthcare providers. The one or more payors can be one or more of, but not limited to, a patient, an insurance company, a health maintenance organization, a healthcare service contractor, a legal entity which is self-insured and provides benefits for healthcare services to employees, a legal entity responsible for handling claims for healthcare services under a medical assistance program, a local government which pays for healthcare services, an insurer authorized to transact workers' compensation or casualty insurance, and an employer authorized to self-insure workers' compensation risk. Accordingly, payors may access the computing device 612 to determine the amount to be paid to the one or more healthcare providers.

In yet another exemplary application, the CARE may be used to provide training to user 610 for facilitating patient-care. The CARE may also be configured on a plurality of computing devices for training a group of users for handling one or more medical conditions in accordance with standard of care clinical protocols or for creating a simulated environment of one or more of a healthcare department, a group of healthcare departments and a hospital. For example, a group of nurses can be trained to provide patient-care according to standard of care clinical protocols for a medical condition by using the multiple bed-side devices to simulate a real-time situation corresponding to the medical condition. Likewise, different nurses can be trained for different medical conditions by simulating real-time situations for the corresponding medical conditions and nurses. Similarly, users of different departments of the hospital can be trained by simulating real-time situations using the CARE configured on client devices of corresponding departments.

System 600 can be accessed in multiple ways for facilitating patient-care with adherence to standard of care clinical protocols as discussed in the various examples and example implementations described above, or as may be apparent to a person of ordinary skill in the art.

Figure 9:
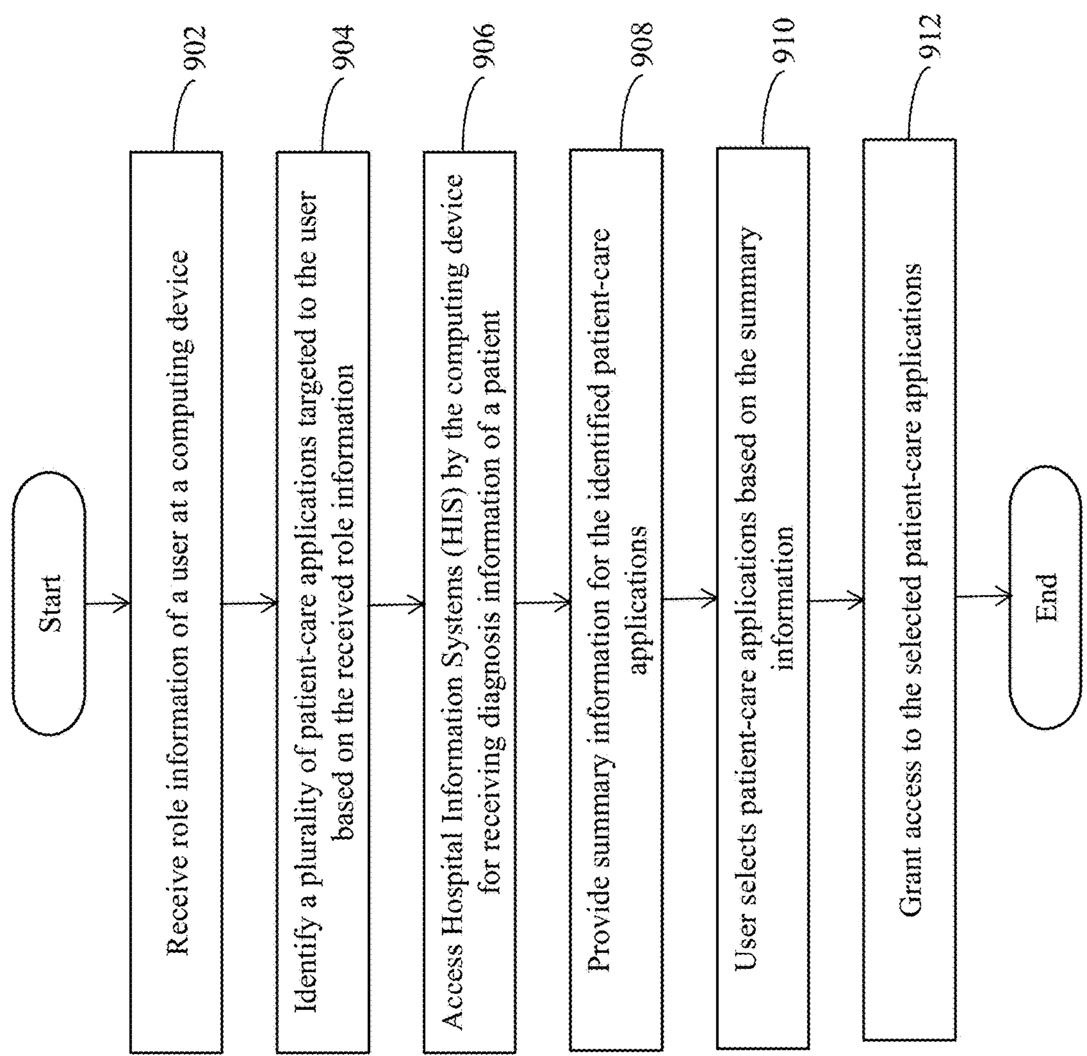
FIG. 9 illustrates a flowchart of a method for facilitating patient-care with adherence to standard of care clinical protocols in accordance with an example implementation of the present application.

FIG. 9 illustrates a flowchart of a method for facilitating patient-care with adherence to standard of care clinical protocols in accordance with an example implementation of the present application.

At step 902, a computing device such as computing device 612 receives role information of a user such as user 610. The role information can be received automatically when user 610 logs on to computing device 612. For example, the login details of user 610 can be used to retrieve the role information of user 610 from a database. Alternately, user 610 can provide the role information by entering details such as, but not limited to, personal identity number, department number, field of expertise, specialization information into the computing device 612. The role information can include one or more, but not limited to, job information, and department information. The job information may provide details regarding user 610's position within a healthcare organization. In some example implementations, the job information may identify a user 610's position as one or more of, but not limited to, a doctor, a nurse, a technician, an administrator, a patient and a payor. The department information may provide details regarding a department associated with user 610 within a healthcare organization. In one implementation, the department information may identify the department associated with user 610 as one or more of, but not limited to, Cardiology, Internal Medicine, OB/GYN, Oncology, Radiology, Surgery, and Pediatrics.

At step 904, a plurality of patient-care applications targeted to user 610 may be identified based on the received role information. In one implementation, computing device 612 identifies the plurality of patient-care applications based on the received role information.

The plurality of patient-care applications can be mobile applications identified from clinical application store 602. Further, the plurality of patient-care applications can include one or more of, but not limited to, condition related applications 620, support applications 622, training applications 624, image viewer applications 626 and laboratory applications 628. For example, if the user 610 is identified as a nurse, then a plurality of nursing related applications may be identified. Similarly, if the user 610 is identified as a cardiologist, then a plurality of cardiology related applications may be identified.

In some example implementations, if the received role information identifies user 610 as a patient, then, optionally at step 906, computing device 612 may accesses the HIS 632 to retrieve one or more of diagnosis information and treatment information associated with user 610. Thereafter, computing device 612 may utilize the retrieved information, in addition to the received role information to identify a plurality of patient-care applications. Optionally, computing device 612 may provide the HIS 632 with information about the identified patient-care applications.

At step 908, summary information for identified patient-care applications is provided to user 610 by computing device 612. The summary information may include a list of the identified patient-care applications. In addition, a brief description of each patient-care application may be provided. Further, the summary information may enable user 610 to select one or more of the identified plurality of patient-care applications. Thereafter, user 610 may be allowed to select one or more of, the patient-care applications listed in the summary information.

At step 910, user 610 may select one or more of the patient-care applications. For example, user 610 can select a plurality of condition based applications listed in the summary information. Selection of the plurality of condition based applications can include selection of, but not limited to, one or more cardiac applications, one or more nephrology applications, one or more respiratory applications, one or more diabetes applications, one or more arthritis applications, one or more asthma applications or any other applications that may be apparent to a person of ordinary skill in the art.

At step 912, the selected patient-care applications may be accessed via network 614 e.g., installed on computing device 612 in order to grant access to the selected applications. User 610 may access the patient-care applications for one or more of, but not limited to, providing input regarding patient medical conditions, receiving output, and receive patient-care instructions and recommendations.

Figure 10:
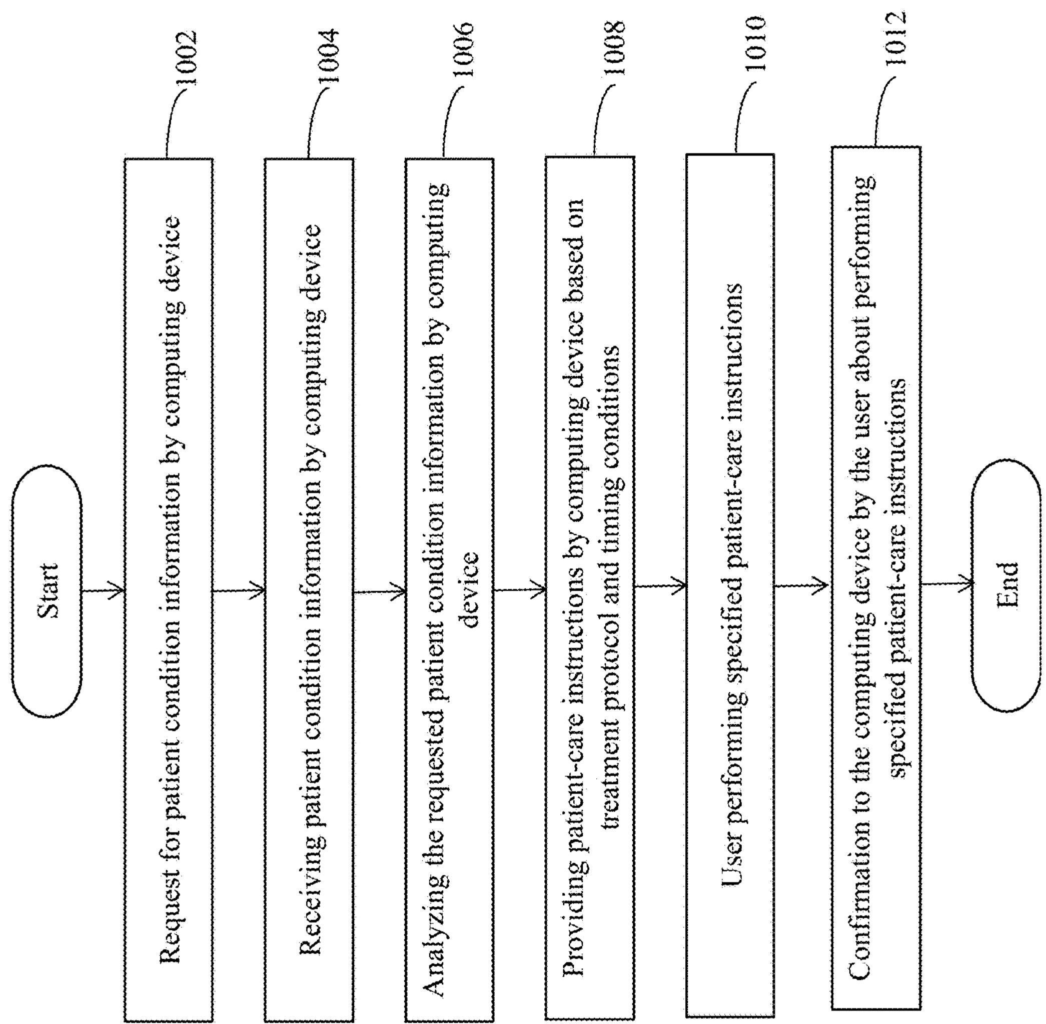
FIG. 10 illustrates a flowchart of a method for facilitating patient-care with adherence to standard of care clinical protocols in accordance with another example implementation of the present application.

FIG. 10 illustrates a flowchart of a method for facilitating patient-care with adherence to standard of care clinical protocols in accordance with another example implementation of the present application.

At step 1002, computing device 612 provides a request to user 610 for providing patient condition information as an input. Computing device 612 provides the request for patient condition information based on one or more of a treatment clinical protocol and the received role information. For example, a request for entering blood pressure information of a patient may be provided to a nurse. Alternately, a request for uploading an x-ray image of a patient may be provided to a radiologist. The request for patient condition information is given to user 610 in one or more ways. For example, the request may be provided on a UI of computing device 612 for entering information. Alternately or additionally, an audio and/or visual alert may be provided indicating that patient condition information is required to be input. Moreover, an email or telephonic message may be sent for requesting the patient condition information.

The instructions may be provided according to the type/configuration of computing device 612. For instance, when computing device 612 is a touch-enabled device such as, but not limited to, a smartphone, a wearable device (such as a smart watch), a tablet, and a notebook, the instructions may be provided such that a touch-screen display of computing device 612 may be used for viewing and completing the instructions. Taking another instance, where computing device 612 includes separate display and input interfaces such as in desktops, the instructions may be rendered via the display of computing device 612 while enabling the corresponding user input from the input interfaces such as, but not limited to, a keypad, a keyboard and a mouse. Taking yet another instance, where computing device 612 is configured to collect input from patient monitors such as, but not limited to, blood pressure sensors and glucose monitors, the configuration can be such that computing device 612 manages the patient monitors for collecting the desired patient data. For example, a wearable device with incorporated sensors may monitor patient vitals or movements using the sensors. It will be apparent that the manner in which instructions are provided and in which user input may be collected need not be limited to the examples provided above and numerous variations would be apparent to those ordinarily skilled in the art.

Providing the request for patient condition information can include transmitting a timing condition to a countdown timer for display. The displayed timing condition as shown in FIG. 11 can specify a length of time within which user 610 needs to provide the requested information. Accordingly, the countdown timer can display the amount of time user 610 has for providing the requested information. For example, the user 610 may be instructed to provide 10 respiratory volume measurements within a 2 minute time frame and a timer could begin counting down. As the end of the countdown approaches additional audio or visual cues may be provided such as alarms, tones, voice instructions, flashing lights, etc. may be provided.

Optionally, the request for providing the patient condition information may include instructing user 610 to attach one or more of patient monitoring units 630 to the patient.

At step 1004, computing device 612, receives the patient condition information as an input. For example, computing device 612 may receive input directly from user 610 via an interface rendered on computing device 612. Taking another example, computing device 612 may receive input from the one or more patient monitoring units. Taking yet another example, computing device 612 may receive input from both user 610 and the one or more patient monitoring units. Optionally, computing device 612 may connect to HIS 632 to update a patient record with the received patient condition information from user 610. Thereafter, at step 1006, computing device 612, analyzes received patient condition information. The analyses may include applying one or more analytical techniques on the received input to identify patient-care instructions. For example, if the input is a text input, natural language processing may be used to analyze the input and identify the patient-care instruction. Similarly, if the input is received from a patient monitoring unit, a signal analysis technique may be utilized to determine the patient condition for identifying the patient-care instructions.

Additionally, an input may also include a confirmation that the recommended steps of treatment were not performed. For example, a user may indicate that a requested number of measurements were not taken, or the recommended procedures were not performed.

Based on the input received, the computing device 612 determines, using algorithms developed based on the standard of care clinical protocol as discussed above, whether the standard of care clinical protocol has been adhered to, whether patient-condition information is within expected values associated with the standard of care clinical protocol, and identifies what additional treatment steps should be performed. For example, in one implementation, a standard of care clinical protocol may require that the patient perform a respiratory volume flow measurement 10 times per hour every hour and that the volume flow meet or exceed a specific volume. If the input indicates that the required measurements are being taken as scheduled and are within the ranges specified by the clinical protocol, the application may recommend continuing the measurements for 7 days without needing to see a doctor. Conversely, if the input indicates that the measurements are only being taken twice per hour and the respiratory volume flow measurements are repeatedly below the required volumes, the application may recommend that patient immediately seek out a respiratory specialist for additional treatment.

At step 1008, computing device 612, provides patient-care instruction to user 610 based on the treatment clinical protocol. Providing patient care instructions may include transmitting instructions such as, but not limited to, take one or more measurements of patient vital signs, obtain one or more patient specimens and perform one or more diagnostic tests (e.g., laboratory tests, imaging tests, etc.) on the one or more patient specimen, perform one or more radiological imaging tests, perform one or more physiological tests and perform one or more medical procedure. Further, providing the patient-care instructions may include providing a timing condition specifying a time period within which the instructions are to be performed by user 610. For example, a count-down timer may be provided counting down the time remaining to perform the specified actions. Further, as the end of the countdown approaches additional audio or visual cues may be provided such as alarms, tones, voice instructions, flashing lights, etc. may be provided. The timing condition as displayed in FIG. 13 can be provided to a count-down timer for displaying the amount of time user 610 has for completing the instruction.

Optionally, computing device 612 may connect with HIS 632 for accessing and correlating additional patient-care information with received patient-care information based on the treatment clinical protocol. Subsequently, the computing device 612 may provide additional patient-care instructions such as, but not limited to, a combination of retrieved additional patient-care information and received patient care information annotated with diagnostic information based on the treatment clinical protocol.

At step 1010, user 610 performs the patient-care instructions provided by computing device 612. User 610 can perform patient-care instructions and recommendations given by computing device 612 in a step-by-step manner as displayed on computing device 612.

Figure 13:
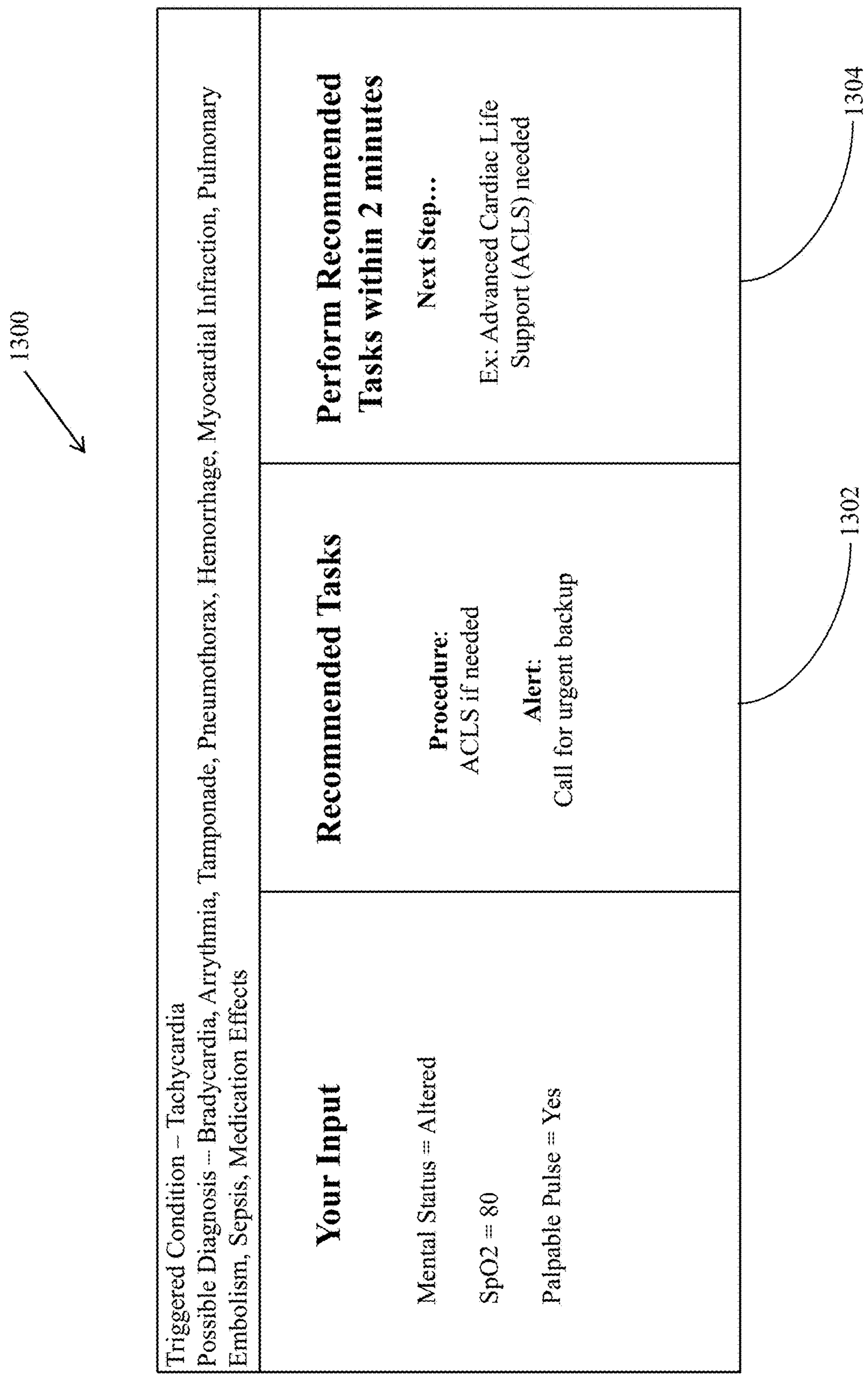
FIG. 13 illustrates a user interface for facilitating patient-care with adherence to standard of care clinical protocols in accordance with a third example implementation of the present application.

User 610 may perform the patient-care instructions in accordance with a timing condition specified by the patient-care instructions. For example, as shown in FIG. 13, a user 610 may provide Advanced Cardiac Life Support (ACLS) within 2 minutes. Alternately, the user 610 may call a cardiac specialist within 2 minutes.

Subsequently, at step 1012, user 610 may provide a confirmation to computing device 610 after performing the patient care-instructions. User 610 provides the confirmation to the computing device 612 by selecting a display button on a UI provided on the computing device 612.

Computing device 612 may also update HIS 632 about patient-care instructions that were transmitted and performed by the user 610 on the patient.

By providing instructions or recommendations of treatment steps to be performed and obtaining feedback input from the user, the computing device 612 can determine if the standard of care clinical protocols are being adhered to in real time and use a recommendation engine to provide recommendations to drive the treatment back to the standard of care clinical protocol if the clinical protocol has been deviated from. Thus, the standard of care clinical protocols can be uniformly applied independent from the role of the user, and independent from the department or location of the user or the patient.

FIGS. 11, 12, and 13 illustrate an example user interfaces used by exemplary applications the method and systems disclosed herein. In accordance with the scenario, assume that a patient with a medical condition of cardiac arrest enters a hospital. A user 610 such as cardiac specialist within healthcare organization may access clinical application store 602 via computing device 612, by providing role information of user 610. Thereafter, one or more appropriate patient-care applications are identified based on the provided role information. Subsequently, the selected patient-care applications are downloaded and installed in computing device 612.

In accordance with the scenario, user 610 can select one of the listed cardiac arrest applications. Accordingly, a selected cardiac arrest application that is installed in computing device 612 provides the simplified user interface (UI) 1100, as illustrated in FIG. 11 for prompting user 610 to input details of a medical condition of the patient. One or more details of medical condition of the patient such as for example, tachycardia, in this scenario, to be entered into an input block 1102 is displayed on UI 1100 of the computing device 612. Accordingly, user 610 provides one or more inputs such as, for example, mental status of the patient, oxygen saturation of the patient, and palpable pulse of the patient into input block 1102.

FIG. 12 illustrates an alternative UI 1200 providing a checklist of actions 1205 to be performed, a countdown timer 1210, links 1215 to protocols applicable to the patient, and other various information applicant to the treatment of the patient.

The simplified UI 1100 of FIG. 11 may be used in situations where the user has a role requiring a minimum amount of information (such as a nurse, intern, etc.), and the complex UI 1200 of FIG. 12 may be used where the user has a role requiring more detailed information (such as intensivist, surgeon, etc.). Alternatively, the simplified UI 1100 of FIG. 11 may be used in situations where there is history of the user not adhering to the protocol to encourage the user to adhere to the protocol. Further, the complex UI 1200 of FIG. 12 may be used in situations where there is history of the user adhering to the protocol. The different UIs may also be used in a variety of other different situations as may be apparent to a person of ordinary skill in the art.

Simultaneously, computing device 612 may also receive information regarding a medical condition of the patient from patient monitoring units 630 that are attached to the patient. The received information is analyzed and an alarm is triggered if a condition trigger specified by a trigger element is met.

Computing device 612 analyzes the details of medical conditions received from user 610 and/or patient monitoring units 630 and displays possible diagnosis information such as, but not limited to, Bradycardia, Arrhythmia, Tamponade, Pneumothorax, Hemorrhage, Myocardial Infraction, Pulmonary Embolism, Sepsis, and Medication Effects. Thereafter depending on one or more diagnosed conditions of the patient and the standard of care clinical protocols for cardiac arrest, the cardiac arrest application displays certain actions, recommendations, instructions and tasks in recommended tasks block 1302 shown in FIG. 13.

Accordingly, user 610 can perform actions as instructed and acknowledge the action using computing device 612. Thereafter, user 610 may be provided with next recommended steps of instructions that are to be performed such as, for example Advanced Cardiac Life Support (ACLS) 1304. It may be apparent that all instructions and recommendations mentioned to user 610 are performed on the patient in accordance with standard of care clinical protocols based on medical conditions.

FIG. 14 illustrates a dashboard UI 1400 that can be used to display a complete overview of a patient's treatment. The dashboard UI 1400 can include a summary of patient information (name, age, diagnosis, treatment, etc.) 1405, patient vitals (HR, BP, SPO2, CVP, etc.) 1410, fluid input/output 1415, prescribed medicine 1420, assigned equipment 1425, and investigations 1430. Further, the Dashboard UI 1400 may also include a summary of adherence to protocols 1435, outstanding orders/follow-up 1440. The Dashboard UI 1400 may also provide links or icons representative of active protocols 1445, and critical warnings 1450.

In some implementations the UIs of FIGS. 11-13 may be controlled and incorporated into a recommendation engine and the UI 1400 of FIG. 14 may be controlled and incorporated into a monitoring engine.

The method and system disclosed herein may facilitate in providing patient-care with adherence to standard of care clinical protocols, which can help to reduce chances of errors in a healthcare environment and improve patient safety. The disclosed method and system may help to enable faster response time to medical conditions of a patient and make decisions for patient-care. As the disclosed method and system may be specific to facilitating patient-care with adherence to standard of care clinical protocols associated with medical conditions, the method and system may assist in improving the quality and consistency of patient care. Thus, favorable outcomes may be a result of utilizing the disclosed method and system. The processes of patient-care may be standardized for handling an event and first line of responses for each medical condition. The disclosed method and system may be user-friendly and may enable healthcare professionals and patients to easily adopt for providing patient-care. The learning curve of a user for patient-care knowledge may also be shortened as the user can be trained on-the-job.

The disclosed system and method may be utilized for providing patient-care to a patient until the patient is clinically fine, as well as after the completion of the clinical care has been completed, to prevent a future recurrence of the clinical condition, or other clinical conditions. The patient-care applications of clinical application store 602 can also be used when the patient is travelling to a healthcare provider, during admission, in the premises of the healthcare provider, or after discharge and at home under observation. Due to easy accessibility to various patient-care applications using clinical application store 602, mortality and morbidity rates may be reduced. Since the patient-care applications are designed using the standard of care clinical protocols specific to a medical condition, the healthcare providers can adhere to the standard of care clinical protocols. The disclosed method and system may also provide a single source for various patient-care actions such as, but not limited to, general investigations, audit, compliance, malpractice investigations, evaluations and quality assurance.

In the foregoing specification, specific example implementations of the present application have been described. However, one of ordinary skill in the art appreciates that various modifications and changes can be made without departing from the scope of the present application as set forth in the claims below. Accordingly, the specification and figures are to be regarded in an illustrative rather than a restrictive sense, and all such modifications are intended to be included within the scope of the present application. The benefits, advantages, solutions to problems, and any element(s) that may cause any benefit, advantage, or solution to occur or become more pronounced are not to be construed as critical, required, or essential features, of the present application.

What is claimed is:

1. A computer-implemented method for facilitating delivery of patient-care, the method comprising:

receiving, by a computing device, patient information indicative of a clinical condition, based on a clinical protocol specific to the clinical condition, the clinical protocol being associated with patient-care instructions specific to an individual patient that must be completed within a time period determined based on the clinical protocol;

providing, by the computing device, the patient-care instructions to a user based on a result of the received patient information;

determining, iteratively by the computing device, adherence to the clinical protocol based on a result of at least one of the providing patient care instructions and the patient information;

based on a result of the determining adherence to the clinical protocol, the computing device automatically determining a recommended action and performing the determined recommended action, wherein the recommended action comprising:

for a determination that the clinical protocol has been adhered to, administering an existing medication to a patient at a first dosage level using an automated medication delivery device; and for a determination that the clinical protocol has not been adhered to, administering the existing medication to the patient at a second dosage level, different from the first dosage level using the automated medication delivery device, the second dosage level being calibrated by the computing device to drive the patient care instructions into compliance with the clinical protocol.

2. The computer-implemented method of claim 1, wherein the receiving patient information comprises specifying that at least one of the patient information be provided and the patient-care instructions be performed within the time period.

3. The computer-implemented method of claim 1, further comprising displaying to the user a count-down timer that is indicative of the time period.

4. The computer-implemented method of claim 1, wherein the providing patient-care instructions comprises at least one of:

taking one or more measurements of patient vital signs;

obtaining one or more patient specimens and performing one or more laboratory tests on the one or more patient specimens;

performing one or more radiological imaging tests on a patient or the one or more patient specimens;

performing one or more physical diagnostic tests on the patient; and performing one or more medical procedures on the patient.

5. The computer-implemented method of claim 1, further comprising:

accessing, by the computing device, a hospital information system to retrieve additional patient information;

correlating, by the computing device, the retrieved additional patient information with the monitored patient information based on the clinical protocol; and wherein the providing the patient-care instructions comprises displaying a combination of the retrieved additional patient information, the monitored patient information, and diagnostic information based on the clinical protocol.

6. The computer-implemented method of claim 1, further comprising receiving role information of the user;

wherein the receiving patient information comprises requesting patient information based on the received role information of the user; and wherein the patient-care instructions are provided based on the received role information of the user.

7. The computer implemented method of claim 1, wherein the patient-care instructions are provided based on a determination of compliance with the standard of care protocol.

8. The computer implemented method of claim 1, wherein the recommended action further comprises automatically sending updated patient instructions for a determination that the clinical protocol has not been adhered to via one or more of:

an email;

an instant message;

a short message service (SMS) message;

a mobile app notification; and a computer generated telephone call.

9. The computer-implemented method of claim 1, further comprising automatically generating a notification that the recommended action has been performed and transmitting the notification to one or more of a member of a patient care team, a health insurance provider, and a care provider system, wherein the notification is sent via one or more of:

an email;

an instant message;

a short message service (SMS) message;

a mobile app notification; and a computer generated telephone call.

10. A non-transitory computer readable medium having stored therein computer executable instructions for causing a computing device to perform the method comprising:

receiving, by a computing device, patient information indicative of a clinical condition, based on a clinical protocol specific to the clinical condition, the clinical protocol being associated with patient-care instructions specific to an individual patient that must be completed within a time period determined based on the clinical protocol;

providing, by the computing device, the patient-care instructions to a user based on a result of the received patient information;

determining, iteratively by the computing device, adherence to the clinical protocol based on a result of at least one of the providing patient care instructions and the patient information; and based on a result of the determining adherence to the clinical protocol, the computing device automatically determining a recommended action and performing the determined recommended action;

wherein the recommended action comprising:

for a determination that the clinical protocol has been adhered to, administering an existing medication to a patient at a first dosage level using an automated medication delivery device; and for a determination that the clinical protocol has not been adhered to, administering the existing medication to the patient at a second dosage level, different from the first dosage level using the automated medication delivery device, the second dosage level being calibrated by the computing device to drive the patient care instructions into compliance with the clinical protocol.

11. The non-transitory computer readable medium of claim 10, wherein the receiving patient information comprises specifying that at least one of the patient information be provided and the patient-care instructions be performed within the time period.

12. The non-transitory computer readable medium of claim 10, further comprising displaying to the user a countdown timer that is indicative of the time period.

13. The non-transitory computer readable medium of claim 10, wherein the providing patient-care instructions comprises at least one of:

taking one or more measurements of patient vital signs;

obtaining one or more patient specimens and performing one or more laboratory tests on the one or more patient specimens;

performing one or more radiological imaging tests on a patient or the one or more patient specimens;

performing one or more physical diagnostic tests on the patient; and performing one or more medical procedures on the patient.

14. The non-transitory computer readable medium of claim 10, further comprising:

accessing, by the computing device, a hospital information system to retrieve additional patient information;

correlating, by the computing device, the retrieved additional patient information with the monitored patient information based on the clinical protocol; and wherein the providing the patient-care instructions comprises displaying a combination of the retrieved additional patient information, the monitored patient information, and diagnostic information based on the clinical protocol.

15. The non-transitory computer readable medium of claim 10, further comprising receiving role information of the user;

wherein the receiving patient information comprises requesting patient information based on the received role information of the user; and wherein the patient-care instructions are provided based on the received role information of the user.

16. The non-transitory computer readable medium of claim 10, wherein the patient-care instructions are provided based on a determination of compliance with the standard of care protocol.

17. The non-transitory computer readable medium of claim 10, wherein the recommended action further comprises automatically sending updated patient instructions for a determination that the clinical protocol has not been adhered to via one or more of:

an email;

an instant message;

a short message service (SMS) message;

a mobile app notification; and a computer generated telephone call.

18. The non-transitory computer readable medium of claim 10, further comprising automatically generating a notification that the recommended action has been performed and transmitting the notification to one or more of a member of a patient care team, a health insurance provider, and a care provider system, wherein the notification is sent via one or more of:

an email;

an instant message;

a short message service (SMS) message;

a mobile app notification; and a computer generated telephone call.

19. A computing device for facilitating delivery of patient-care, the computing device comprising a storage device; and a processor configured to perform:

receiving patient information indicative of a clinical condition, based on a clinical protocol specific to the clinical condition, the clinical protocol being associated with first patient-care instructions and second patient-care instructions specific to an individual patient that each must be completed within a time period determined based on the clinical protocol;

providing the first patient-care instructions to a first user based on a result of the monitoring;

determining, iteratively, adherence to the clinical protocol based on a result of at least one of the providing the first patient care instructions and the patient information; and based on a result of the determining adherence to the clinical protocol, automatically determining a first recommended action and performing the determined first recommended action;

wherein the first recommended action comprises:

for a determination that the clinical protocol has been adhered to, controlling an automated medication delivery device to administer an existing medication to a patient at a first dosage level; and for a determination that the clinical protocol has not been adhered to, controlling the automated medication delivery device to administer the existing medication to the patient at a second dosage level, different from the first dosage level, the second dosage level being calibrated by the processor to drive the patient care instructions into compliance with the clinical protocol.

20. The computing device of claim 19, wherein the recommended action further comprises automatically sending updated patient instructions for a determination that the clinical protocol has not been adhered to via one or more of:

an email;

an instant message;

a short message service (SMS) message;

a mobile app notification; and a computer generated telephone call.

* * * * *